US010517591B2

(12) United States Patent
Olson et al.

(10) Patent No.: US 10,517,591 B2
(45) Date of Patent: Dec. 31, 2019

(54) SURGICAL STAPLER WITH UNIVERSAL ARTICULATION AND TISSUE PRE-CLAMP

(71) Applicant: Covidien LP, Mansfield, MA (US)

(72) Inventors: Lee Ann Olson, Wallingford, CT (US); Philip Roy, Lafayette, CO (US); John W. Beardsley, Wallingford, CT (US); Ralph Stearns, Bozrah, CT (US); David C. Racenet, Killingworth, CT (US); Clifford J. Emmons, Dennis, MA (US)

(73) Assignee: Covidien LLP, Mansfield, MA (US)

( * ) Notice: Subject to any disclaimer, the term of this patent is extended or adjusted under 35 U.S.C. 154(b) by 0 days.

(21) Appl. No.: 16/354,737

(22) Filed: Mar. 15, 2019

(65) Prior Publication Data

US 2019/0209166 A1 Jul. 11, 2019

Related U.S. Application Data

(63) Continuation of application No. 16/032,239, filed on Jul. 11, 2018, which is a continuation of application
(Continued)

(51) Int. Cl.
*A61B 17/068* (2006.01)
*A61B 17/072* (2006.01)
(Continued)

(52) U.S. Cl.
CPC ...... *A61B 17/068* (2013.01); *A61B 17/07207* (2013.01); *A61B 17/072* (2013.01);
(Continued)

(58) Field of Classification Search
CPC ............ A61B 17/068; A61B 17/07207; A61B 17/072; A61B 2017/07214;
(Continued)

(56) References Cited

U.S. PATENT DOCUMENTS 3,079,606 A 3/1963 Bobrov et al.
3,490,675 A 1/1970 Green et al.
(Continued)

FOREIGN PATENT DOCUMENTS

DE 2744824 A1 4/1978
DE 2903159 A1 7/1980
(Continued)

OTHER PUBLICATIONS

Australian Patent Examination Report dated Jun. 30, 2015 in connection with corresponding Australian Patent Application No. 2012268848.
(Continued)

*Primary Examiner* — Michelle Lopez
(74) *Attorney, Agent, or Firm* — Carter, DeLuca & Farrell LLP

(57) ABSTRACT

A tool assembly for a surgical stapling device includes a channel member for supporting a staple cartridge therein and an anvil to deform a plurality of staples ejected from the staple cartridge thereagainst. The tool assembly also includes a sled which is movable to force the staples from the cartridge against the anvil to staple tissue disposed between the anvil and the staple cartridge. A dynamic clamping member is included which has a pin which movably engages the anvil and a flange which movably engages the channel assembly. The dynamic clamping member is mounted to and movable with the sled. The pin and the flange of the dynamic clamping member cooperating to oppose the forces associated with clamping and stapling tissue and also to maintain a substantially uniform gap between the anvil and the staple cartridge during stapling of the tissue.

20 Claims, 20 Drawing Sheets

Related U.S. Application Data

No. 13/855,166, filed on Apr. 2, 2013, now Pat. No. 10,130,360, which is a continuation of application No. 13/553,926, filed on Jul. 20, 2012, now abandoned, which is a continuation of application No. 11/998,035, filed on Nov. 28, 2007, now Pat. No. 8,596,513, which is a continuation of application No. 10/529,799, filed as application No. PCT/US03/31716 on Oct. 6, 2003, now Pat. No. 7,726,537.

(60) Provisional application No. 60/416,372, filed on Oct. 4, 2002.

(51) Int. Cl.
*A61B 17/32* (2006.01)
*A61B 17/29* (2006.01)

(52) U.S. Cl.
CPC ........... *A61B 2017/07214* (2013.01); *A61B 2017/07278* (2013.01); *A61B 2017/07285* (2013.01); *A61B 2017/2927* (2013.01); *A61B 2017/2929* (2013.01); *A61B 2017/2932* (2013.01); *A61B 2017/2939* (2013.01); *A61B 2017/320024* (2013.01); *A61B 2017/320052* (2013.01)

(58) Field of Classification Search
CPC .. A61B 2017/0278; A61B 2017/07285; A61B 2017/2927; A61B 2017/2929; A61B 2017/2932; A61B 2017/2939
USPC ...................................... 227/176.1
See application file for complete search history.

(56) References Cited

U.S. PATENT DOCUMENTS

| | | |
|---|---|---|
| 4,429,695 A | 2/1984 | Green |
| 4,473,077 A | 9/1984 | Noiles et al. |
| 4,482,197 A | 11/1984 | Ouellette et al. |
| 4,505,414 A | 3/1985 | Filipi |
| 4,520,817 A * | 6/1985 | Green ............... A61B 17/07207 206/339 |
| 4,566,620 A | 1/1986 | Green et al. |
| 4,580,712 A | 4/1986 | Green |
| 4,589,413 A | 5/1986 | Malyshev et al. |
| 4,602,634 A | 7/1986 | Barkley |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,892,244 A | 1/1990 | Fox et al. |
| 4,978,049 A | 12/1990 | Green |
| 4,991,764 A | 2/1991 | Mericle |
| 5,040,715 A | 8/1991 | Green et al. |
| 5,065,929 A | 11/1991 | Schulze et al. |
| 5,074,454 A | 12/1991 | Peters |
| 5,083,695 A | 1/1992 | Foslien et al. |
| 5,084,057 A | 1/1992 | Green et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,170,925 A | 12/1992 | Madden et al. |
| 5,246,156 A | 9/1993 | Rothfuss et al. |
| RE34,519 E | 1/1994 | Fox et al. |
| 5,282,807 A | 2/1994 | Knoepfler |
| 5,307,976 A | 5/1994 | Olson et al. |
| 5,312,023 A * | 5/1994 | Green ............... A61B 17/07207 227/175.1 |
| 5,318,221 A | 6/1994 | Green et al. |
| 5,326,013 A | 7/1994 | Green et al. |
| 5,328,077 A | 7/1994 | Lou |
| 5,332,142 A | 7/1994 | Robinson et al. |
| 5,336,232 A | 8/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,376,095 A | 12/1994 | Ortiz |
| 5,381,943 A | 1/1995 | Allen et al. |
| 5,382,255 A | 1/1995 | Castro et al. |
| 5,383,880 A | 1/1995 | Hooven |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,533,521 A | 7/1996 | Granger |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,573,543 A | 11/1996 | Akopov et al. |
| 5,575,799 A | 11/1996 | Bolanos et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |

(56) References Cited

U.S. PATENT DOCUMENTS

| | | |
|---|---|---|
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,269 A | 11/1997 | Bolanos et al. |
| 5,692,668 A | 12/1997 | Schulze et al. |
| 5,697,542 A | 12/1997 | Knodel et al. |
| 5,704,534 A | 1/1998 | Huitema et al. |
| 5,709,334 A | 1/1998 | Sorrentino et al. |
| 5,711,472 A | 1/1998 | Bryan |
| 5,713,505 A | 2/1998 | Huitema |
| 5,716,366 A | 2/1998 | Yates |
| 5,725,536 A | 3/1998 | Oberlin et al. |
| 5,725,554 A | 3/1998 | Simon et al. |
| 5,728,110 A | 3/1998 | Vidal et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,897,562 A | 4/1999 | Bolanos et al. |
| 5,901,895 A | 5/1999 | Heaton et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,954,259 A * | 9/1999 | Viola .............. A61B 17/07207 227/176.1 |
| 5,980,510 A | 11/1999 | Tsonton et al. |
| 6,004,335 A | 12/1999 | Vaitekunas et al. |
| 6,010,054 A | 1/2000 | Johnson et al. |
| 6,032,849 A | 3/2000 | Mastri et al. |
| 6,079,606 A | 6/2000 | Milliman et al. |
| 6,109,500 A | 8/2000 | Alli et al. |
| 6,119,913 A | 9/2000 | Adams et al. |
| 6,197,017 B1 | 3/2001 | Brock et al. |
| 6,202,914 B1 | 3/2001 | Geiste et al. |
| 6,231,565 B1 | 5/2001 | Tovey et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,830,174 B2 | 12/2004 | Hillstead et al. |
| 6,835,119 B2 | 12/2004 | Hori |
| 6,835,199 B2 * | 12/2004 | McGuckin, Jr. ........................... A61B 17/07207 606/142 |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,986,451 B1 | 1/2006 | Mastri et al. |
| 7,055,730 B2 | 6/2006 | Ehrenfels et al. |
| 7,128,253 B2 | 10/2006 | Mastri et al. |
| 7,159,750 B2 | 1/2007 | Racenet et al. |
| 7,278,563 B1 | 10/2007 | Green |
| 8,596,513 B2 | 12/2013 | Olson et al. |
| 2002/0004498 A1 | 1/2002 | Doherty et al. |
| 2002/0009193 A1 | 1/2002 | Deguchi |
| 2002/0018323 A1 | 2/2002 | Li et al. |
| 2002/0032948 A1 | 3/2002 | Ahn et al. |
| 2002/0036748 A1 | 3/2002 | Chapoy et al. |

(56) References Cited

U.S. PATENT DOCUMENTS

| | | |
|---|---|---|
| 2002/0045442 A1 | 4/2002 | Silen et al. |
| 2002/0069565 A1 | 6/2002 | Liao |
| 2002/0069595 A1 | 6/2002 | Knudson et al. |
| 2002/0084304 A1 | 7/2002 | Whitman |
| 2002/0111621 A1 | 8/2002 | Wallace et al. |
| 2002/0117533 A1 | 8/2002 | Milliman et al. |
| 2002/0143346 A1 | 10/2002 | McGuckin et al. |
| 2002/0177843 A1 | 11/2002 | Anderson et al. |
| 2002/0188294 A1 | 12/2002 | Couture et al. |
| 2002/0190093 A1 | 12/2002 | Fenton |
| 2003/0009193 A1 | 1/2003 | Corsaro |
| 2003/0105476 A1 | 6/2003 | Sancoff et al. |
| 2003/0132268 A1 | 7/2003 | Whitman |
| 2004/0004105 A1 | 1/2004 | Jankowski |
| 2004/0007608 A1 | 1/2004 | Ehrenfels et al. |
| 2004/0050902 A1 | 3/2004 | Green et al. |
| 2004/0093029 A1 | 5/2004 | Zubik et al. |
| 2004/0094597 A1 | 5/2004 | Whitman et al. |
| 2004/0108357 A1 | 6/2004 | Milliman et al. |
| 2004/0149802 A1 | 8/2004 | Whitman |
| 2004/0173659 A1 | 9/2004 | Green et al. |
| 2004/0199181 A1 | 10/2004 | Knodel et al. |
| 2004/0232199 A1 | 11/2004 | Shelton et al. |
| 2004/0232200 A1 | 11/2004 | Shelton et al. |
| 2004/0232201 A1 | 11/2004 | Wenchell et al. |
| 2004/0243151 A1 | 12/2004 | Demmy et al. |
| 2004/0267310 A1 | 12/2004 | Racenet et al. |
| 2005/0006429 A1 | 1/2005 | Wales et al. |
| 2005/0006430 A1 | 1/2005 | Wales |
| 2005/0006431 A1 | 1/2005 | Shelton et al. |
| 2005/0006432 A1 | 1/2005 | Racenet et al. |
| 2005/0006433 A1 | 1/2005 | Milliman et al. |
| 2005/0006434 A1 | 1/2005 | Wales et al. |
| 2005/0023324 A1 | 2/2005 | Doll et al. |
| 2005/0023325 A1 | 2/2005 | Gresham et al. |
| 2005/0067457 A1 | 3/2005 | Shelton et al. |
| 2005/0067458 A1 | 3/2005 | Swayze et al. |
| 2005/0067459 A1 | 3/2005 | Swayze et al. |
| 2005/0067460 A1 | 3/2005 | Milliman et al. |
| 2005/0072827 A1 | 4/2005 | Mollenauer |
| 2005/0103819 A1 | 5/2005 | Racenet et al. |
| 2005/0119669 A1 | 6/2005 | Demmy |
| 2005/0127131 A1 | 6/2005 | Mastri et al. |
| 2006/0011699 A1 | 1/2006 | Olson et al. |
| 2006/0016853 A1 | 1/2006 | Racenet |
| 2007/0034670 A1 | 2/2007 | Racenet et al. |
| 2007/0108252 A1 | 5/2007 | Racenet et al. |

FOREIGN PATENT DOCUMENTS

| | | |
|---|---|---|
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0621006 A1 | 10/1994 |
| EP | 0621009 A1 | 10/1994 |
| EP | 0640317 A1 | 3/1995 |
| EP | 0656188 A2 | 6/1995 |
| EP | 0666057 A2 | 8/1995 |
| EP | 0705570 A1 | 4/1996 |
| EP | 0705571 A1 | 4/1996 |
| EP | 0741996 A2 | 11/1996 |
| FR | 2542188 A1 | 9/1984 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| SU | 659146 A1 | 4/1979 |
| SU | 728848 A1 | 4/1980 |
| SU | 980703 A1 | 12/1982 |
| SU | 990220 A1 | 1/1983 |
| WO | 8302247 A1 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 0230297 A2 | 4/2002 |

OTHER PUBLICATIONS

European Office Action corresponding to European Application No. 10 007 933.4 dated Oct. 28, 2015 and European Search Report for corresponding EP 10 00 7 933, date of completion is Sep. 23, 2010 (3pages).

European Search Report dated Sep. 1, 2016, issued in EP Application No. 16173306.

European Search Report dated Mar. 27, 2017, issued in EP Application No. 16204896.

European Office Action dated May 3, 2018 in EP Appln. No. 15 170 873.

European Search Report for EP 07023879.5-1265 date of completion is Jan. 28, 2008 (6 pages).

European Search Report for corresponding EP 10 00 7905, date of completion is Sep. 22, 2010 (3 pages).

* cited by examiner

SURGICAL STAPLER WITH UNIVERSAL ARTICULATION AND TISSUE PRE-CLAMP

CROSS REFERENCE TO RELATED APPLICATIONS

This application is a continuation of U.S. patent application Ser. No. 16/032,239, filed Jul. 11, 2018, which is a continuation of U.S. patent application Ser. No. 13/855,166, filed Apr. 2, 2013, now U.S. Pat. No. 10,130,360, which is a continuation of U.S. patent application Ser. No. 13/553,926, filed Jul. 20, 2012, now abandoned, which is a continuation of U.S. patent application Ser. No. 11/998,035, filed Nov. 28, 2007, now U.S. Pat. No. 8,596,513, which is a continuation of U.S. patent application Ser. No. 10/529,799, filed Mar. 30, 2005, now U.S. Pat. No. 7,726,537, which is a U.S. National Stage Application filed under 35 U.S.C. § 371(a) of International Patent Application Serial No. PCT/US03/31716, filed Oct. 6, 2003, which claims priority from U.S. Provisional Pat. App. Ser. No. 60/416,372, filed Oct. 4, 2002. Each of these applications is incorporated herein by reference in its entirety.

BACKGROUND

1. Technical Field

This application relates to a surgical stapling apparatus, and more particularly, to an articulating endoscopic surgical stapling apparatus which sequentially applies a plurality of surgical fasteners to body tissue and subsequently incises the fastened tissue.

2. Background of Related Art

Surgical devices wherein tissue is first grasped or clamped between opposing jaw structure and then joined by surgical fasteners are well known in the art. Typically, a knife is employed after the tissue is fastened to cut the tissue along a preferred cutting path. The fasteners are typically in the form of surgical staples but other types of fasteners can also be utilized to accomplish the same or similar purpose.

Instruments for this purpose can include two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars or sleds that have cam surfaces that travel longitudinally through the staple cartridge and staple pushers that sequentially eject the staples from the staple cartridge. Typically, a knife travels between the staple rows to longitudinally cut and/or open the stapled tissue between the rows of formed staples.

One of the issues associated with prior stapler designs is the tendency for the dynamic clamping member to skew or buckle as it passes through the tissue due to the large forces generated during stapling and cutting tissue. For example, prior dynamic clamping member designs that carry the knife or cutting surface provide cantilever-like designs which are designed to effectively squeeze tissue ahead of the knife blade and the staple forming sled to force fluids from the tissue which enhances tissue stapling and contributes to a successful tissue staple. However, the large forces required to staple and incise tissue tend to place undue stresses on the cantilever knife design which may cause the knife to skew or buckle during translation often requiring the surgeon to fire the stapler very slowly through larger tissue structures to avoid the possibility of the knife traveling off line.

It is an object of this disclosure to provide a surgical stapler having an actuator, preferably, a dynamic clamping member which enhances tissue stapling by forcing fluids out of the clamped tissue before ejecting stapling into and stapling the tissue. Another object of this disclosure is to provide a dynamic clamp member that applies substantially clamping pressure upon the anvil and cartridge assembly of the tool member of a surgical stapler as the dynamic clamping member translates along and through the tool assembly.

Another object of this disclosure is to provide a dynamic clamping member that helps to provide a uniform tissue gap between the tissue contacting surfaces of an anvil and a staple cartridge in the immediate area of and during sequential, progressive staple formation and tissue fastening, as well as in the area of and during tissue cutting, if cutting is being performed.

SUMMARY

The present disclosure relates to a tool assembly for a surgical stapler, which tool assembly includes a channel member for supporting a staple cartridge therein and an anvil for deforming a plurality of staples pushed from the staple cartridge thereagainst. At least one sled is included which moves from a first position out of operative engagement with the plurality of staples or staple pushers to a subsequent positions which progressively and sequentially force the staples from the staple cartridge through the tissue disposed in the gap between the anvil and the staple cartridge and against the anvil such that the staples deform and staple or fasten the tissue. Typically and preferably, the sled includes at least one angled surface which upon movement thereof engages staple pushers that force the staples from the staple cartridge and against the anvil.

The present disclosure also includes a dynamic clamping member which is movable with the sled and which includes a first mechanical interface which engages the anvil and a substantially opposed second mechanical interface which engages the channel assembly. The first and second mechanical interfaces of the dynamic clamping member are in substantial vertical registration relative to one another to oppose the forces associated with damping and stapling tissue and to maintain a substantially uniform gap between the anvil and the staple cartridge during stapling. Preferably, the first mechanical interface of the dynamic clamping member includes a pin which translates within a corresponding slot disposed within the anvil upon movement of the clamp assembly. The second mechanical interface of the dynamic damping member preferably includes a central support or upward extension which translates within a corresponding slot disposed within the channel assembly upon movement of the dynamic clamping member. Advantageously, the pin and the flange are dimensioned to oppose the forces associated with the sled forcing the plurality of staples against the anvil to staple tissue disposed therebetween.

In one embodiment, the tool assembly includes a selectively movable clamping collar which biases against a cam surface on the anvil to close the anvil relative to the staple cartridge and grasp tissue therebetween.

Another embodiment according to the present disclosure relates to an articulating assembly for a surgical stapling device which includes an elongated shaft having proximal and distal ends and a longitudinal "X" axis defined therethrough. The shaft is selectively rotatable about the longitudinal "X" axis. The articulating assembly also includes a tool assembly which attaches to the distal end of the shaft and includes a tube adapter which pivotably mounts a pivot block to allow pivotable movement of the tool assembly about a "Y" axis defined perpendicular to the "X" axis and a "Z" axis define perpendicular to the "X" axis.

Preferably, the tool assembly also includes an anvil having a bottom surface and a channel assembly to support a staple cartridge therein. The staple cartridge includes a plurality of staples therein and a tissue contacting upper surface which opposes the bottom surface of the anvil. A movable sled is also included which has at least one angled surface which is designed to force the plurality of staples to deform against the bottom surface of the anvil. The tool assembly also includes a dynamic clamping member which moves with the sled to sever tissue after deformation of the staples against the anvil. Preferably, rotation of the shaft about the longitudinal "X" axis correspondingly rotates the tool assembly about the longitudinal "X" axis.

In another embodiment, the tool assembly includes a selectively movable clamping collar which biases against a cam surface on the anvil to close the anvil relative to the staple cartridge to grasp tissue therebetween.

In another embodiment, the dynamic damping member includes a first mechanical interface which translates within a corresponding slot disposed within the anvil upon movement of the sled and a second mechanical interface which translates within a corresponding slot disposed within the channel assembly upon movement of the sled. Preferably, the first mechanical interface includes a pin and the second mechanical interface includes a flange or plate. Advantageously, the pin and the flange or plate are dimensioned and/or positioned to oppose the forces associated with deforming the plurality of staples against the anvil to staple tissue disposed therebetween. These forces include those associated with the resistance of compression of the tissue, and squeezing and movement or flow of fluid within the tissue.

The present disclosure also relates to a tool assembly for a surgical stapling device which includes an anvil having a longitudinally disposed slot defined therethrough and a channel assembly which also has a longitudinally disposed slot also defined therethrough. A staple cartridge having a plurality of staples disposed therein mechanically mounts to the channel assembly. A sled is included preferably as part of the tool assembly and which is selectively movable along the staple cartridge to force the plurality of staples to deform against a bottom surface of the anvil. The dynamic clamping assembly can include a bottom camming surface or member, e.g., a flange, and an upwardly extending support or extension which extends upwardly from the bottom flange.

Preferably, the upwardly extending support or extension includes a leading cutting edge for severing tissue and an aperture defined through the dynamic clamping member for receiving a pin therein. The pin is advantageously configured to ride along the slot defined within the anvil and the bottom flange is advantageously configured to mount through the sled and into the slot defined within the channel assembly. Movement of the sled moves the dynamic clamping member not only to staple tissue through the staple cartridge but preferably also to sever tissue after stapling it.

The pin and the bottom flange of the dynamic clamping member are better positioned to cooperatively oppose the forces associated with clamping and stapling tissue and maintain a substantially uniform gap between the anvil and the staple cartridge during progressive stapling as the dynamic clamping member translates along the tool assembly. Preferably, the tool assembly includes a selectively movable clamping collar which biases against a cam surface on a proximal portion of the anvil to close or pre-clamp the anvil relative to the staple cartridge to grasp tissue therebetween.

BRIEF DESCRIPTION OF THE DRAWINGS

Various embodiments of the subject instrument are described herein with reference to the drawings wherein.

DETAILED DESCRIPTION

Figure 1A:
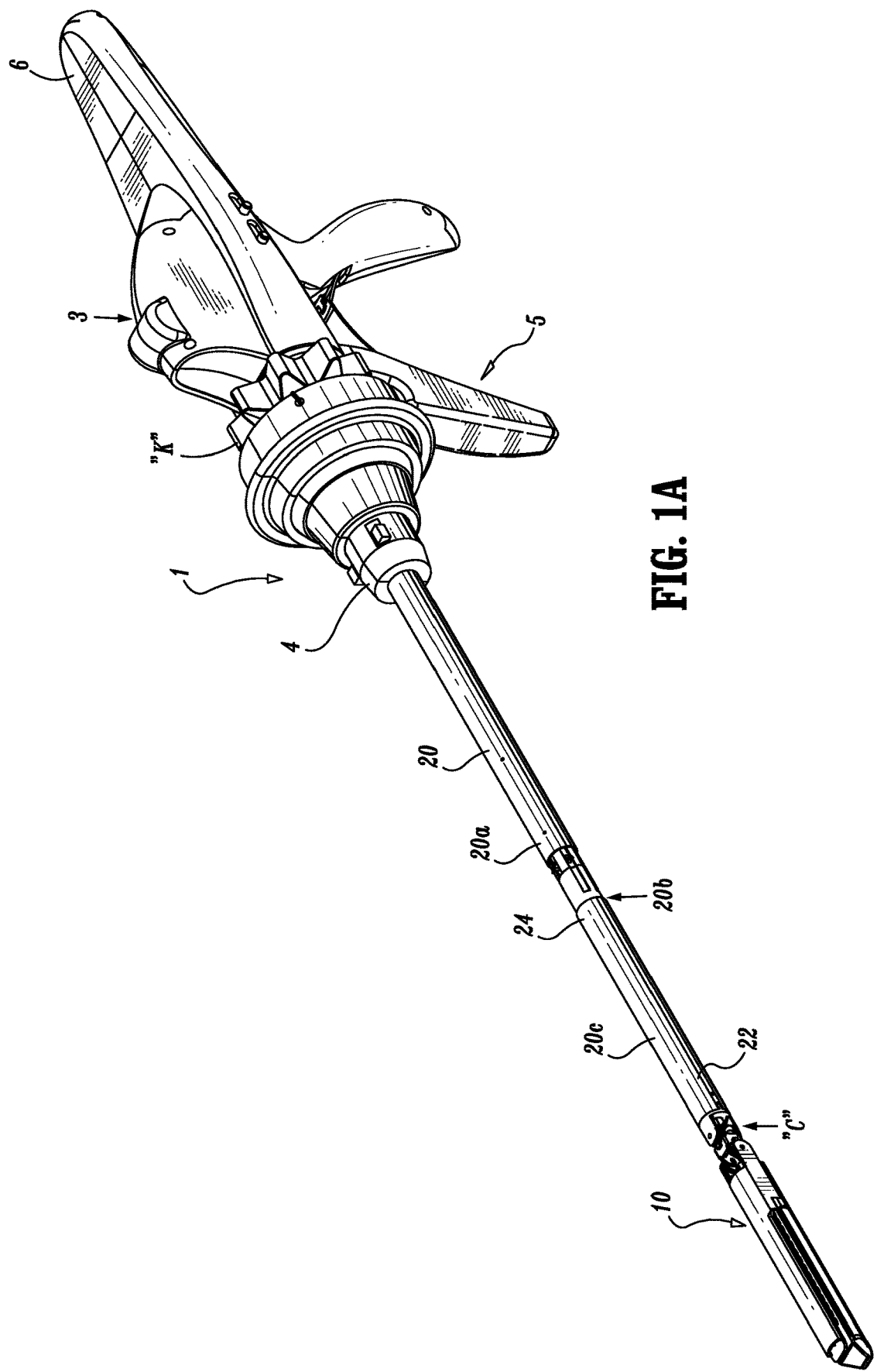
FIG. 1A is a perspective view of a surgical stapler for use with a tool assembly according to the present disclosure.
Figure 1B:
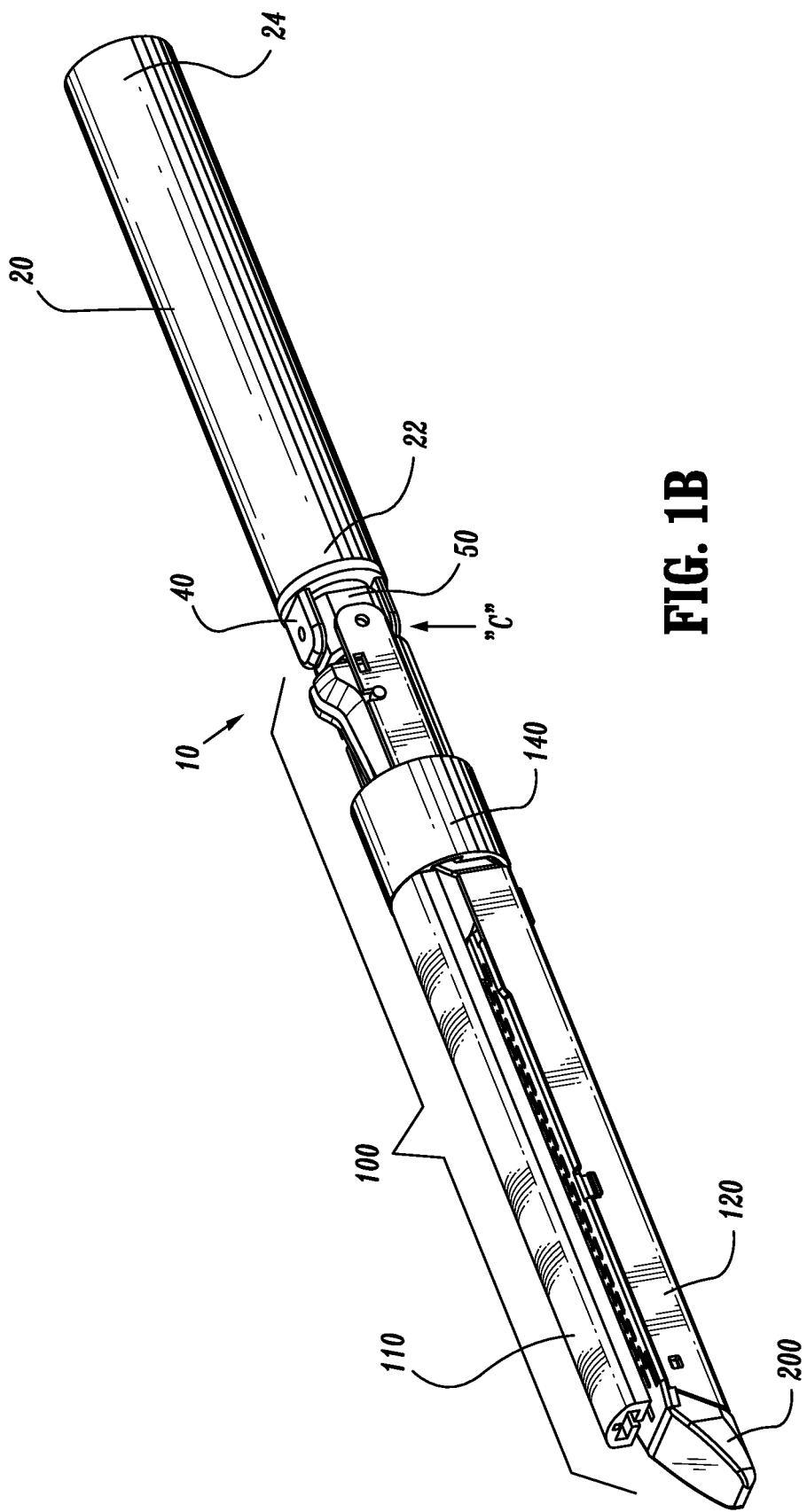
FIG. 1B is a perspective view of the tool assembly of the surgical stapler according to the present disclosure.

FIG. 1A shows a surgical stapler, generally designated 1, for use in various open, endoscopic or laparoscopic surgical procedures. Stapler 1 includes a housing 3 having distal and proximal ends 4 and 6, respectively, an elongated shaft 20 mounted to housing 3, preferably to its distal end 4, and a handle assembly generally designated 5. Shaft 20 has a distal end 20a to which is operatively attached by attachment mechanism 20b to a disposable loading unit 10. As also shown in FIG. 1B, disposable loading unit (DLU) 10 is comprised of a tool assembly 100 and a shaft connector portion 20c which are pivotally and operatively attached to each other through connector mechanism C. Shaft connector portion 20c is removably operatively attached to proximal end 24 of distal end 20a of shaft 20.

It is within the scope of this disclosure that tool assembly 100 may be pivotally, operatively, integrally attached, for example, through a connection mechanism such as C permanently and directly to distal end 20a of shaft 20 of a disposable surgical stapler. As is known, a used or spent disposable loading unit 10 can be removed from shaft 20 of a reusable or reposable open, endoscopic or laparoscopic surgical stapler, and replaced with an unused disposable unit. It is contemplated that shaft 20 with or without an integral or removably attached disposable loading unit can be selectively removable from housing 3.

Shaft connector portion 20 includes a proximal end 24 and a distal end 22. As mentioned above, the proximal end 24 is can be permanently or removably associated with a handle or other actuating assemblies of a manually (or other, e.g., robotic or computer) operated open or endoscopic surgical stapler 1 (or system—not shown). Distal end 22 of shaft connector portion 20 is operatively connected to tool assembly 100. Tool assembly 100, in general, includes a cartridge channel assembly 120, an anvil assembly 110 and a staple cartridge assembly 200. Tool assembly 100 also includes an actuator, preferably a dynamic clamping member 150, a sled 160, as well as staple pushers 228 and staples 350 once an unspent or unused cartridge 200 is in or mounted in channel assembly 120.

In the drawings and in the descriptions which follow, the term "proximal", as is traditional, will refer for example to the end of tool assembly 100 which is closer to the user, while the term "distal" will refer to the end which is further from the user.

Figure 9:
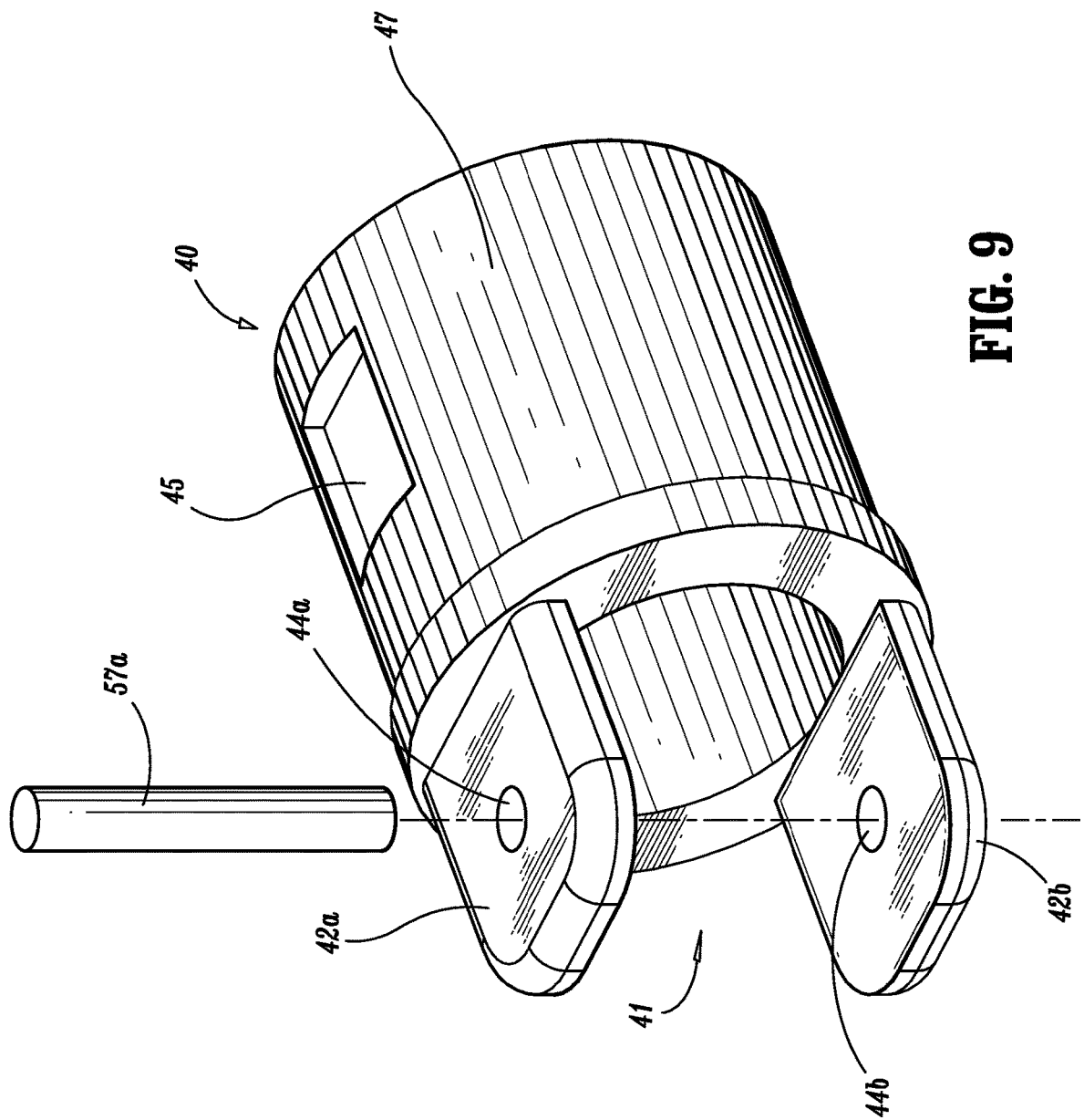
FIG. 9 is a side, perspective view of an adapter for mounting the pivot block to the shaft of the surgical stapler

Shaft connector portion 20c is preferably cylindrical and defines an internal channel 25 at the distal end 22 thereof and which is dimensioned to receive a tube adapter or adapter 40 which will be described in more detail with respect to FIG. 9 below. Shaft connector portion 20c also receives or houses actuators for actuating tool assembly 100. As best shown in FIGS. 1A, 1B, 2 and 9, tool assembly 100 mounts to distal end 22 of shaft connector 20c (or the distal end 20a of shaft 20). Commonly owned U.S. application Ser. No. 60/479,379 includes one possible design of a stapler with a tool assembly mounted thereto, the entire contents of this application being incorporated by reference herein.

More particularly, tool assembly 100 is mounted onto tube adapter 40 which includes an outer cylindrical surface 47 that is slidingly received in friction-fit engagement and attached to internal housing 25 of shaft connector 20c (or, again, to shaft 20). Herein, the description of the proximal connection or attachment of tool assembly 100 to shaft connector 20c also applies to its connection to shaft 20. Preferably, the outer surface 47 of the tube adapter 40 includes at least one mechanical interface, e.g., a cutout or notch 45, which mates with a corresponding mechanical interface, e.g., a radially inwardly extending protrusion or detent (not shown), disposed on the inner periphery of internal housing 25 to lock the tube adapter 40 to the shaft connector 20c. As a result, rotation of shaft 20 about an "X" axis defined with respect to tool assembly 100 (See FIG. 3) correspondingly rotates tool assembly 100 in the same direction.

As best shown in FIGS. 1B, 3, 4, 8 and 9, the distal end of tube adapter 40 includes a pair of opposing flanges 42a and 42b which define a cavity 41 for pivotably receiving a pivot block 50 therein. More particularly, each flange 42a and 42b includes an aperture 44a and 44b (FIG. 8) defined therein which receives pivot pin 57 (FIG. 4) also received in apertures 52a, 52b of pivot block 50 to allow pivotable movement of pivot block 50 about a "Z" axis defined as perpendicular to longitudinal axis "X" of tool assembly 100 (See FIGS. 3 and 8).

Figure 3:
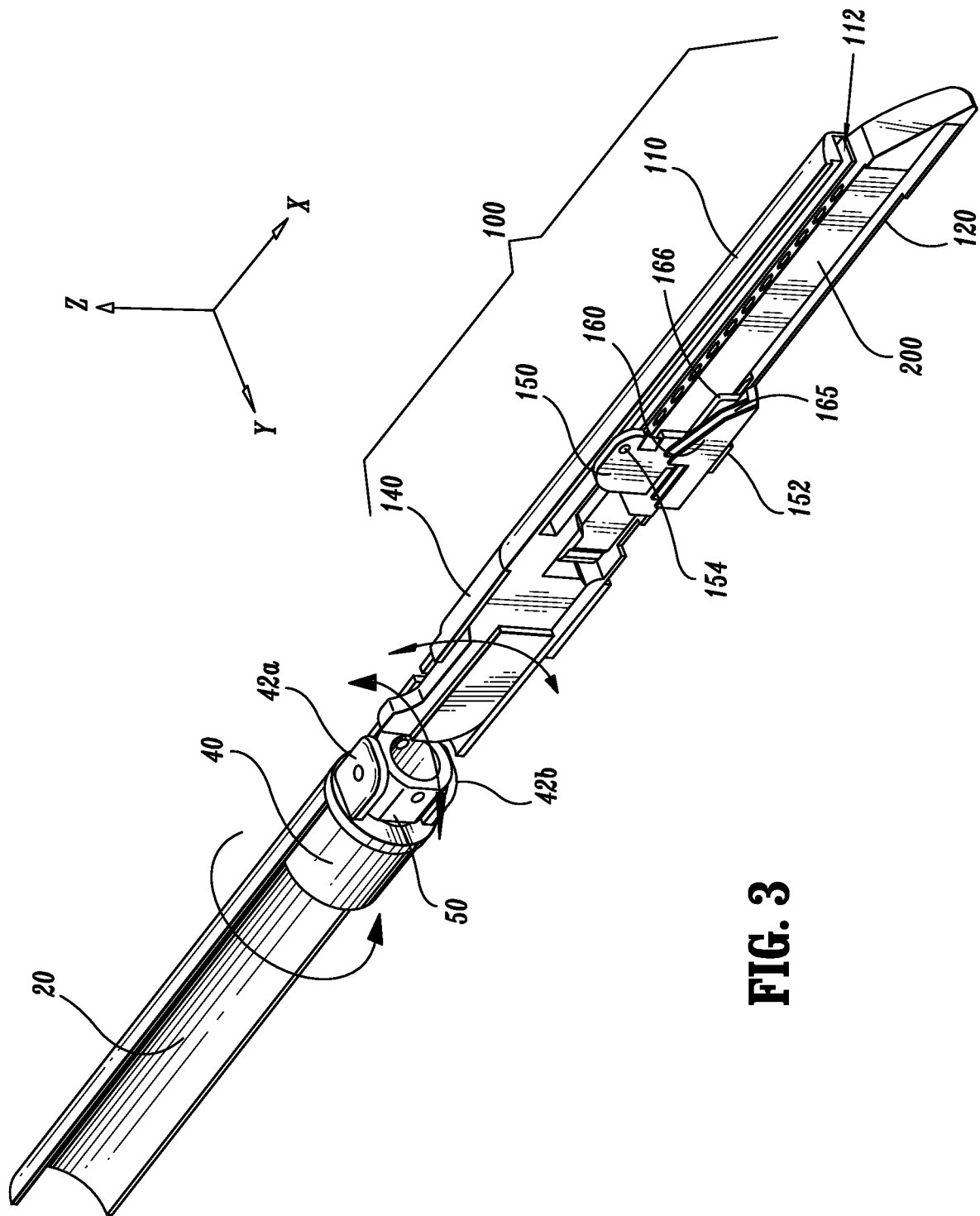
FIG. 3 is a right, perspective cross section of the tool assembly of FIG. 1 showing internal components thereof.
Figure 6A:
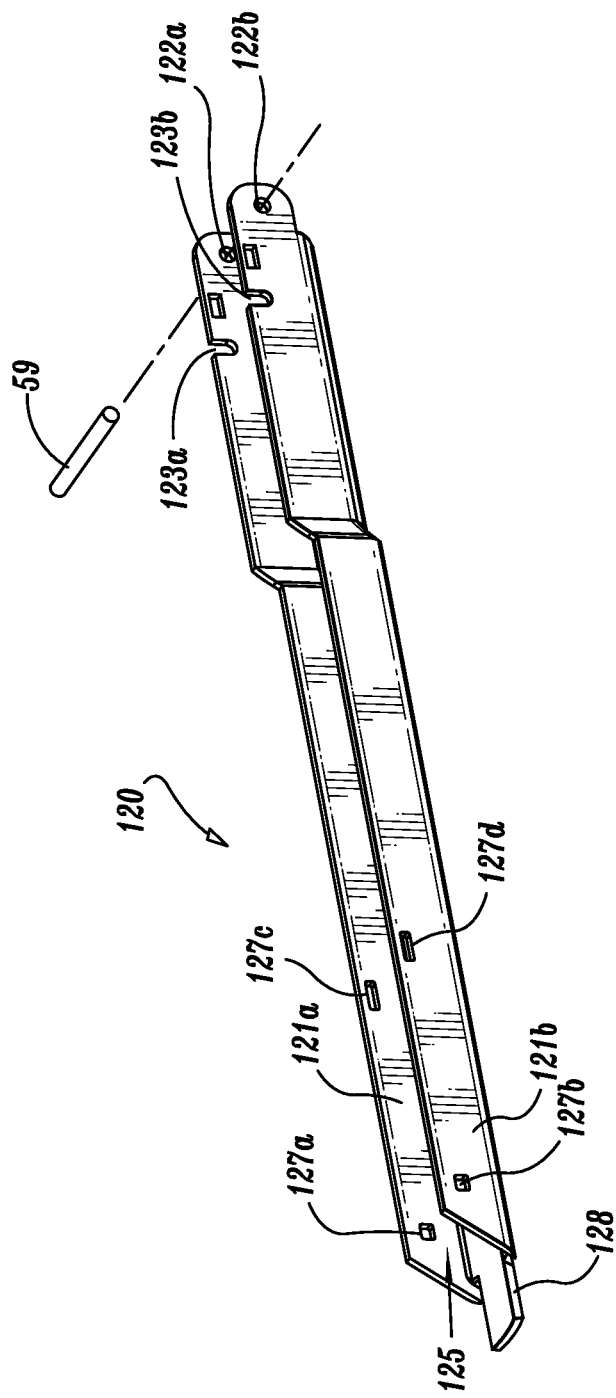
FIG. 6A is a side, perspective view of a channel assembly for supporting a staple cartridge according to the present disclosure.
Figure 8:
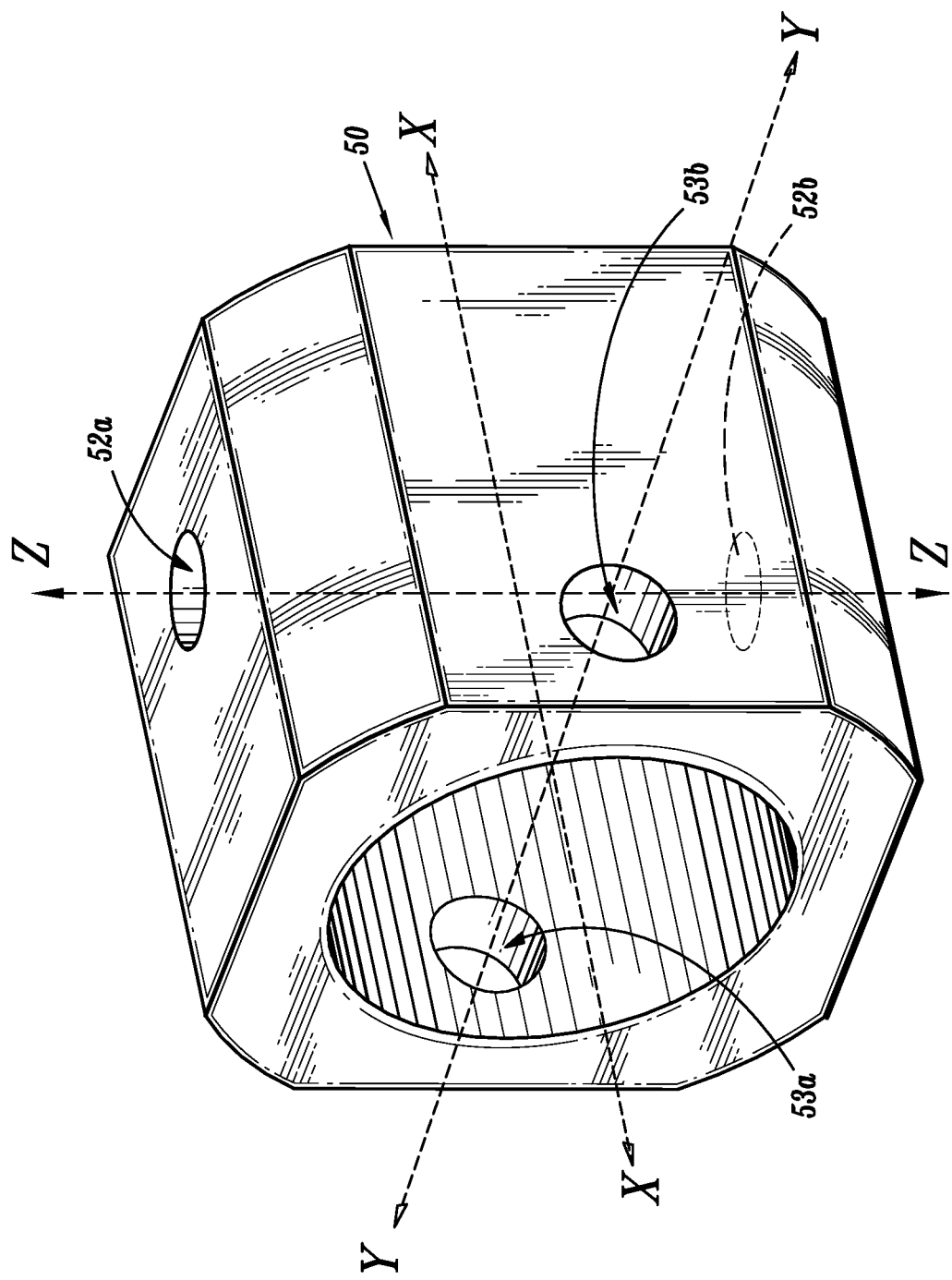
FIG. 8 is a side, perspective view of a pivot block which mounts the tool assembly to a shaft of the surgical stapler to permit articulation of the tool assembly relative to the shaft.

As explained in more detail below in the description of the channel assembly 120, the proximal end of each upwardly extending flange 121a and 121b of the channel assembly 120 includes a pair of apertures 122a and 122b disposed therethrough which are dimensioned to receive a pivot pin 59 (FIG. 6A). In turn, pivot pin 59 mounts through apertures 53a, 53b of pivot block 50 to permit rotation of the tool assembly 100 about the "Y" axis as needed during a given surgical procedure (FIGS. 3 and 8).

An actuator or a plurality of actuators (not shown) preferably pass through shaft connector portion 20c, tube adapter 40 and pivot block 50 and operably connect to tool assembly 100 to permit the surgeon to articulate tool assembly 100 about the "Y" and "Z" axes as needed during a surgical procedure. In addition, shaft 20 of surgical stapler 1 is rotatable 3600 by the rotation of knob "K". As a result, tool assembly 100 is articulatable at least 90 degrees in all directions. Various actuators, hand assemblies and pivot blocks are envisioned which can be utilized to accomplish this task some of which are identified in commonly-owned U.S. Pat. Nos. 6,250,532 and 6,330,965 and U.S. Provisional Application Ser. No. 60/479,379 filed on Jun. 17, 2003 entitled "Surgical Stapling Device, the entire contents of all of which are hereby incorporated by reference herein.

Figure 2:
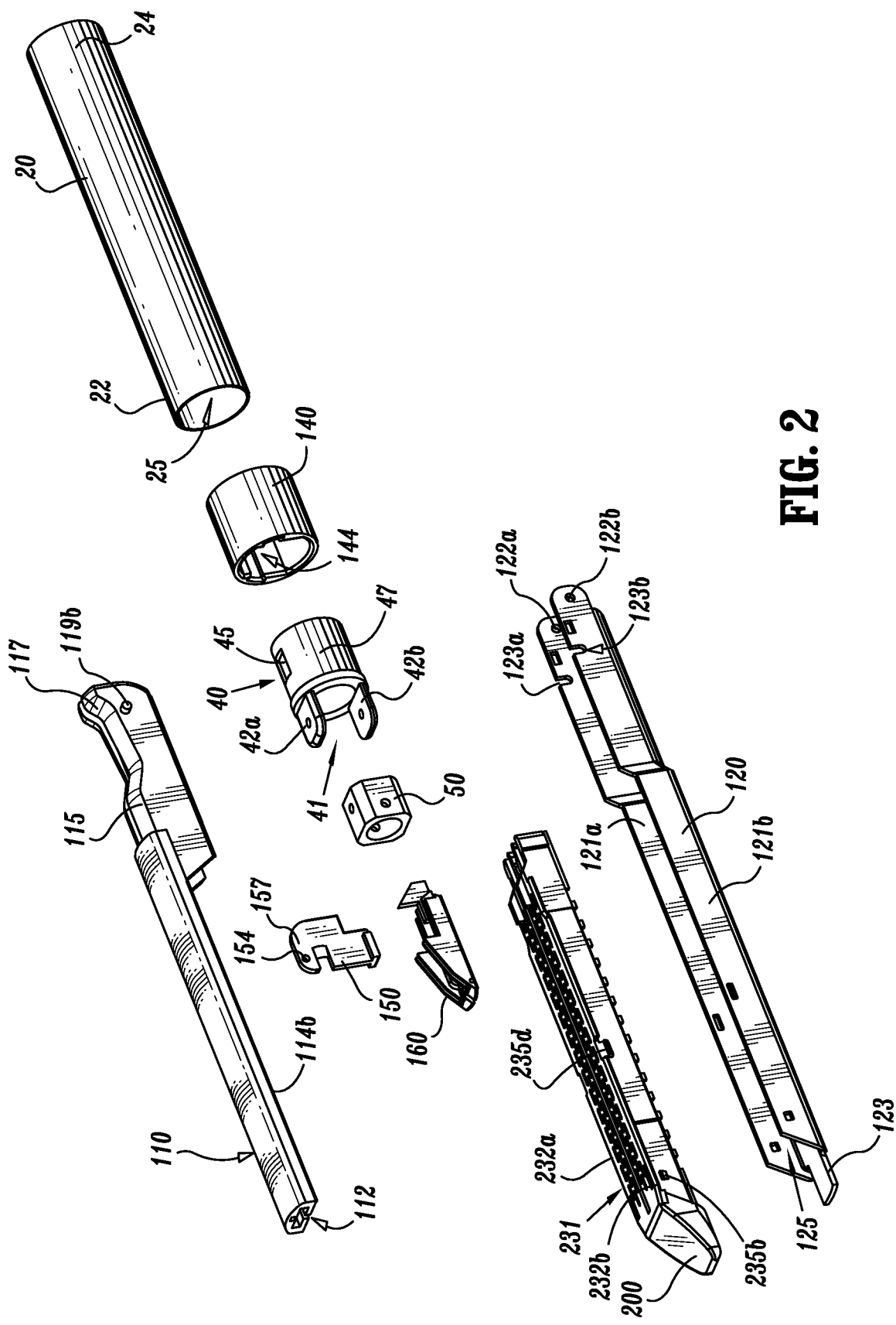
FIG. 2 is an exploded view of the tool assembly of FIG. 1.

As best seen in FIGS. 1B and 2 and as mentioned above, tool assembly 100 includes anvil assembly 110 and channel assembly 120. Channel assembly 120 supports staple cartridge assembly 200, an actuator, e.g., a dynamic clamping member 150, and a sled 160. As such, these various assemblies and their respective internal components, when assembled, cooperate to allow the tool assembly to manipulate, grasp, clamp, fasten and, preferably, sever tissue 400 during a given surgical procedure as explained below.

Generally, the top and bottom halves of a portion of tool assembly 100 are defined by anvil assembly 110 and cartridge channel assembly 120. Staple cartridge assembly 200 mounts within channel assembly 120 and includes an upper tissue contacting or facing surface 231 which opposes a tissue contacting or facing bottom anvil surface 114b of anvil assembly 110. As best seen in FIG. 1B, anvil assembly 110 and channel assembly 120 (and, thus, when mounted, staple cartridge assembly 200) are pivotably coupled near the proximal end of tool assembly 100 to allow anvil assembly 110 to pivot with respect to channel assembly 120 (and staple cartridge assembly 200). More particularly, anvil assembly 110 and channel assembly 120 are pivotably coupled with respect to one another by two mechanical elements, namely, upwardly extending flanges 121a and 121b of channel assembly 120 and pre-clamping collar 140.

More particularly, the proximal end of each sidewall or upwardly extending flange 121a and 121b of channel assembly 120 includes a cut out, e.g., cul de sac 123a, 123b, which are configured to pivotably receive a pair of corresponding protrusions or detents 119a (not shown) and 119b which extend laterally from the proximal end of the anvil assembly 110. This allows the anvil assembly 110 to pivot with respect to the channel assembly 120.

Pre-clamping collar 140 is designed to encompass and clamp or preferably pre-clamp the channel assembly 120 and the anvil assembly 110 together in an approximated and clamp position prior to tissue fastening. As can be appreciated, by moving pre-clamping collar 140 distally the user can actuate/move the anvil assembly 110 from an open, first position toward channel assembly 120 to approximate the jaws, i.e., the anvil 110 and cartridge 200, to a second, closed position to grasp tissue 400 therebetween. The sled 160 can be actuated by the user to staple and subsequently incise the tissue 400. The details of sled 160, dynamic clamping member 150 and the staple cartridge assembly 200 are described in further detail below. Pre-clamp is understood to mean that damping collar 140 approximates and damps the anvil and cartridge assemblies from or at the proximal end portions before stapling and before dynamic damping member 150 (or 150") subsequently progressively clamps the anvil and cartridge assemblies in the area of stapling and preferably cutting tissue as the dynamic damping member translates through the tool assembly 100.

As best seen in FIGS. 7A, 7C, 11B and 11D, sled 160 includes a pair of upwardly-extending cam wedges 161a and 161b (See FIG. 7A) which, when actuated to move by the user, cam a series of surgical fasteners 500 or staples (See FIG. 11D) into and through the tissue 400 (FIG. 11B) and against staple forming pockets 111 of anvil assembly 110 to deform the fasteners 350 and fasten tissue 400 therewith. Dynamic damping member 150 is associated with, e.g., mounted on and rides on, or with or is connected to or integral with and/or rides behind sled 160. It is envisioned that dynamic damping member 150 can have cam wedges or cam surfaces attached or integrally formed or be pushed by a leading distal surface thereof As shown, dynamic clamping member 150 is disposed or seated in sled 160 behind upwardly-extending wedges 161a and 161b such after the surgical fasteners 500 are fired and formed against anvil bottom surface 114b, the dynamic clamping member 150 severs tissue 400 between the two rows of fasteners 500. Details of the various above-mentioned subassemblies and components of the tool assembly 100 and the inter-cooperating features among all the same are described in more detail below with respect to the corresponding figure drawings.

As shown in FIGS. 1B, 2, 4, 5, 6A and 11B, anvil assembly 110 preferably is elongated and includes a proximal end 116, a distal end 118 and top and bottom surfaces 114a and 114b, respectively. As explained above, a pair of rocker pins 119a (not shown) and 119b are disposed near proximal end 116 and are designed for pivotable engagement with corresponding pair of cutouts 123a and 123b defined within the sidewalls 121a, 121b near the proximal end of the channel assembly 120. It is contemplated that actuation by conventional means (e.g., activated remotely; e.g., by a handle assembly 5 (FIG. 1A)) will cause clamping collar 140 to move in a distal direction and engage forward cam surface 115 of anvil assembly 110. This will cause the anvil assembly 110 to pivot from an open first position wherein the anvil assembly 110 and the channel assembly 120 are disposed in spaced relation relative to one another to a second closed position wherein anvil assembly 110 and staple cartridge assembly 120 cooperate to grasp tissue 400 therebetween, i.e., pre-clamp the tissue between tissue engaging surface 114b of anvil and opposing tissue engaging surface 231 of staple cartridge assembly 200.

More particularly, it is envisioned that the initial grasping or pre-clamping of tissue essentially squeezes or forces fluids laterally and axially from the tissue 400 thus reducing the likelihood of the staples being hydraulically displaced during staple deformation. Movement of clamping collar 140 proximally over proximal cam surface 117 will pivot anvil assembly 110 about pins 119a, 119b to open the anvil assembly 110 relative to the staple cartridge assembly 200. In accordance with this disclosure the grasping, i.e., clamping of tissue by clamping collar 140 is referred to as pre-clamping the tissue, i.e., before the dynamic clamping member subsequently clamps, preferably, further damps or compresses, tissue.

Preferably, anvil assembly 110 is made from a suitable heavy gauge material such as, e.g., 301 surgical stainless steel (or other high-strength and durable material) to resist the forces of staple ejection and formation against the anvil bottom surface 114b and especially at the distal end portion of the anvil assembly 110, and to resist the forces associated with tissue expansion an/or fluid flow within the tissue during pre-clamping damping collar 140 and subsequently damping by dynamic damping member 150, 150" as well as during the fastening and cutting processes. The use of the heavy gauge material for the anvil assembly 110 allows aperture 154 and camming pin 159 of the presently disclosed dynamic clamping member 150 to be advantageously positioned in substantial vertical registration with bottom flange 152 of damping assembly 150.

Figure 14:
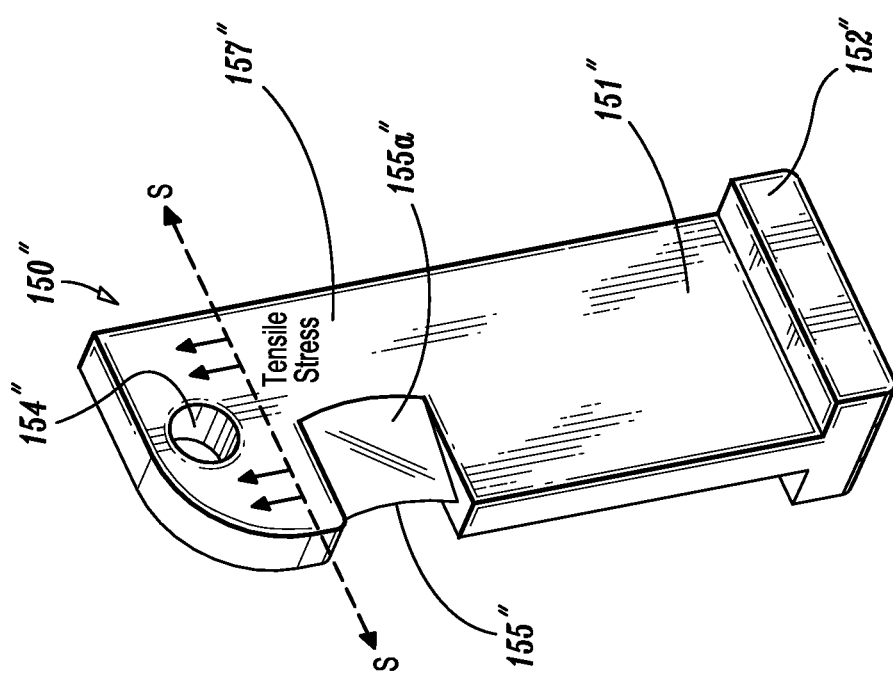
FIG. 14 is a perspective view of an alternate dynamic clamping member design according to the present disclosure.

As shown in FIG. 14, the heavy gauge material of the anvil assembly 110 allows an improved different dynamic damping member 150" (or dynamic damping member 150 of FIG. 10) to be utilized. The design of dynamic damping member 150" greatly reduces any tendency of the clamping assembly 150 buckling due to opposing compressive and tensile forces since as shown in FIG. 14, there is only tensile stress along line "S" due to the bottom flange 152" and the upper camming pin 159 (See FIG. 10) in aperture 154" being disposed in substantial vertical registration relative to one another.

Figure 4:
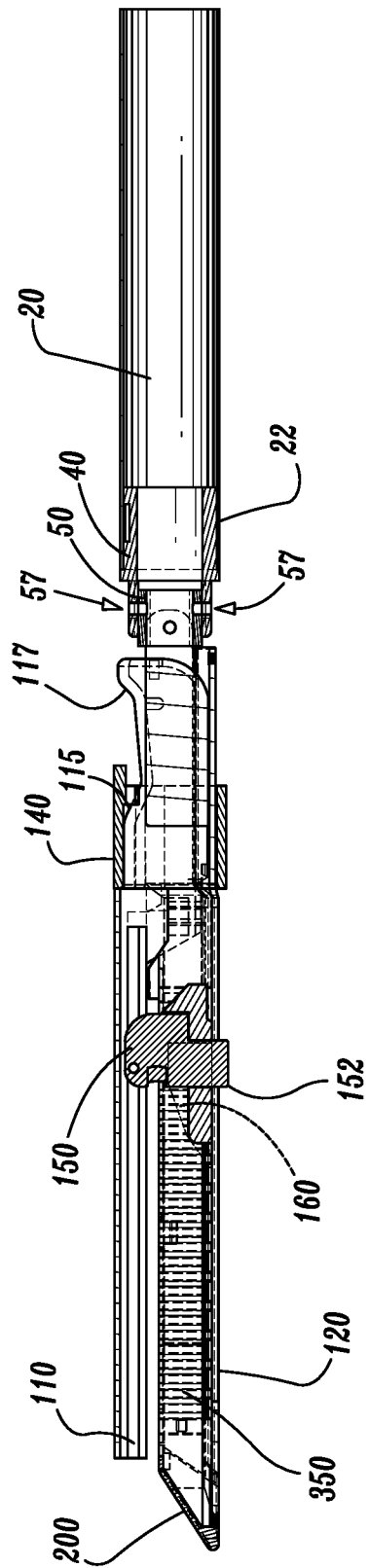
FIG. 4 is a left, side, partial cross sectional view showing a dynamic clamping member according to the present disclosure.
Figure 11A:
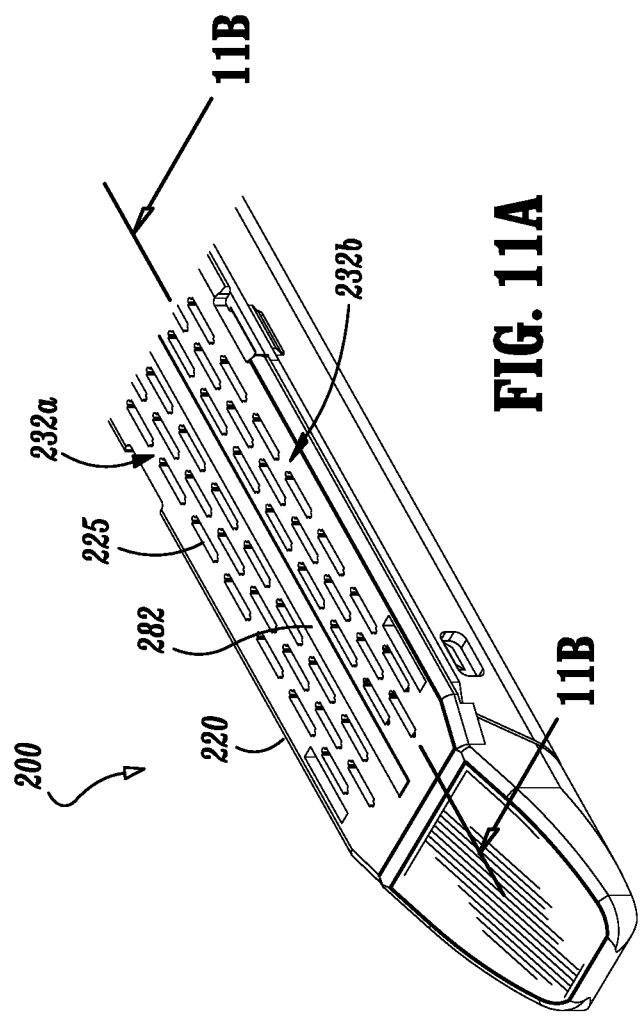
FIG. 11A is a front perspective view of a distal end of a staple cartridge for use in accordance with the present disclosure.
Figure 11B:
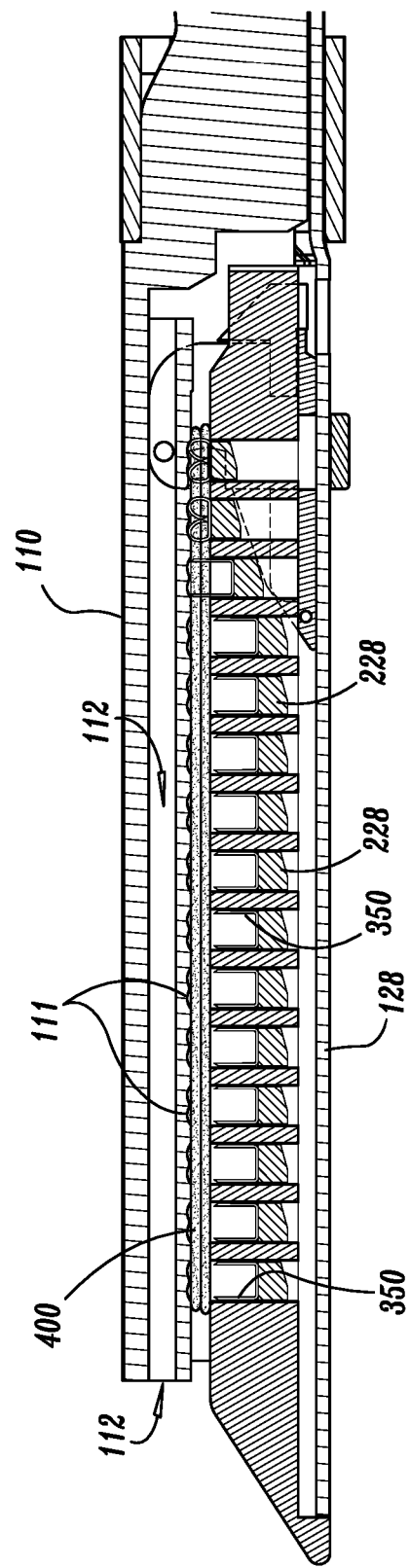
FIG. 11B is a side, cross sectional view of the tool assembly shown in FIG. 1B and the cartridge assembly shown in FIG. 11A.

As a result and as best illustrated by FIGS. 4 and 11B, during distal translation of the dynamic damping member 150 or 150" through tissue 400, the combination of the heavy gauge material of the anvil assembly 110 and the substantially vertical alignment of the flange 152, knife edge 155 and camming pin 159 disposed in aperture 154 operate to further proximate (i.e., further clamp) the opposing tissue engaging surfaces (i.e., anvil bottom surface 114b and upper facing surface 231 of staple cartridge assembly 200) at a moving point which is distal to the leading edge 155 of the knife 155a. The further damping of the tissue distally relative to the translating dynamic clamping member 150 acts to maintain a maximum acceptable gap between the opposing surface 114b and 231 and forces fluid from the tissue 400 which enhances stapling and reduces the likelihood of hydraulically displacing the staples 500 during deformation.

It is also envisioned that utilization of a heavy gauge material for both anvil assembly 110 and pre-clamping collar 140 will also provide an enhanced clamping pressure along the length of tissue 400 and help to provide a uniform gap between the respective approximated anvil assembly 110 and cartridge 200 prior to firing the stapler and translating the sled 160 and dynamic damping member 150 through the tissue 400. Moreover, utilizing pre-clamping collar 140 to pre-damp tissue 400 prior to deformation of the staples 500, also tends to force some tissue fluid distally and axially outwardly which again reduces the likelihood of hydraulically displacing staples 500 during deformation to fasten tissue 400.

After tissue 400 is fastened and severed (as explained in more detail below with respect to the operation of the dynamic clamping member 150), the operator can release pre-clamping collar 140 through re-activation or reverse activation of the damping actuator (not shown). As explained above, the operator actuates the clamping actuator to move the pre-damping collar 140 proximally against rear cam surface 117 which, in turn, forces anvil assembly 110 to pivot to an open position about rocker pins 119*a* and 119*b*.

Figure 5:
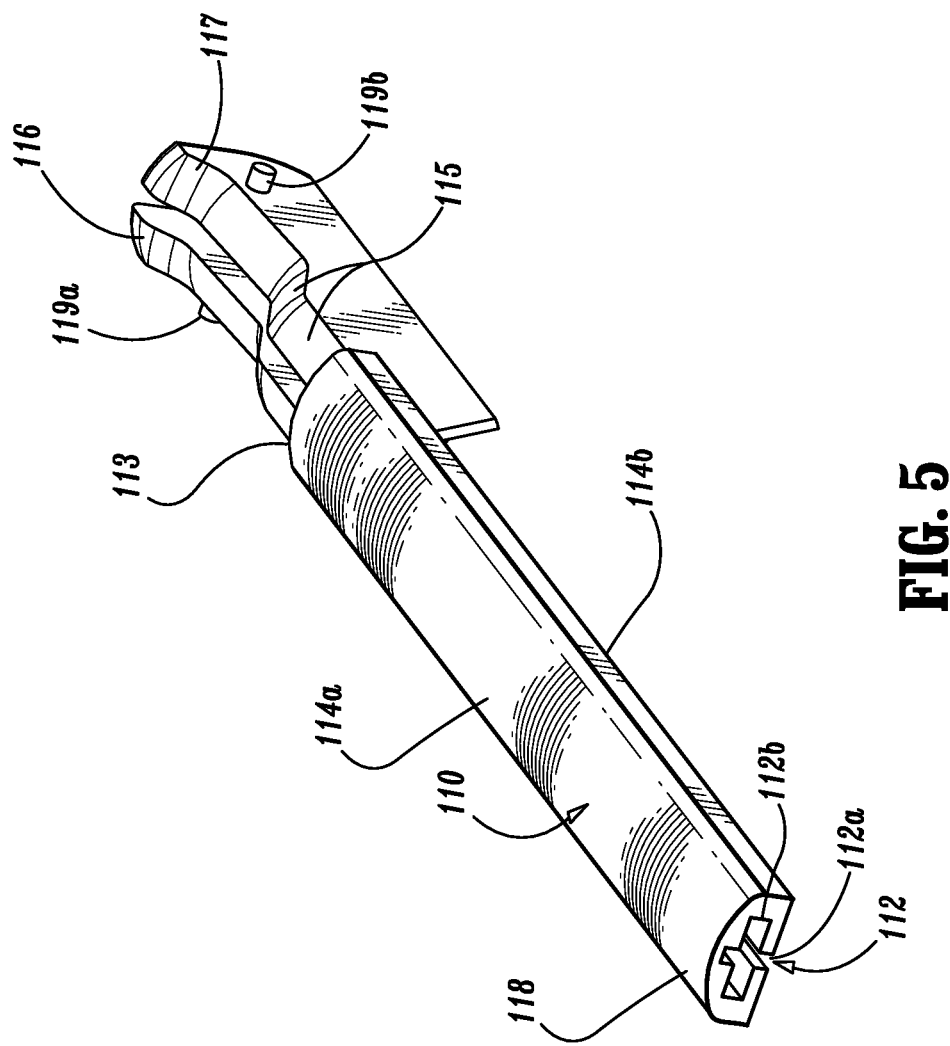
FIG. 5 is a top, perspective view showing an anvil for forming a series of surgical fasteners according to the present disclosure.

As best shown in FIG. 5, anvil assembly 110 includes an elongated cross or T-shaped channel or slot generally designated 112 having a depending central portion or leg 112*a* and a transverse upper portion 112*b*. Slot 112 preferably extends longitudinally from proximal end 113 of upper portion 114*a* of the anvil assembly 110 to the distal end 118 thereof. Leg 112*a* starts from or enters proximate end 113 of anvil assembly 110 and extends to distal end 118 and upper transverse portion 112*b* starts proximate cam 115 and extends to distal end 118. Preferably, upper portion 112*b* is dimensioned to slidingly receive transverse pin 159 that extends within aperture 154 in upper portion 157 of central support or extension 157 of dynamic damping member 150 (see FIG. 10). Pin 159 is dimensioned to slidingly lock the upper portion 157 of dynamic clamping member 150 within the T-shaped channel 112 such that the dynamic clamping member 150 is longitudinally-reciprocable within slot 112.

As mentioned above, the pin 159 and channel 112 arrangement of the dynamic damping member 150 in the anvil assembly 110 and the arrangement of the bottom flange through slot 126 in channel assembly 120 (FIG. 6B) assures that dynamic damping member 150 and its knife blade travel between the surgical fasteners 500 along an ideal transverse and vertical cutting plane through the tissue 400. That is, the pin 159—slot 112 and flange 152—slot 126 arrangements prevent the dynamic damping member 150 from skewing, i.e., laterally displacing the anvil assembly 110 relative to staple cartridge assembly 200 (either vertically ("Z" axis") or transversely ("Y" axis)) during the fastening and severing processes. Moreover and as explained above, these arrangements also counteract the clamping forces associated with compression of tissue in the gap between anvil assembly 110 and cartridge assembly 120 and the ejection and deformation of the staples 500 to keep the anvil assembly 110 and the staple cartridge assembly 200 in substantially uniform and close relation relative to one another during the progressive, sequential deformation of staples 500 and incision of the tissue 400 as dynamic clamping member 150 moves from the proximal to distal ends of the anvil assembly 110, channel assembly 120 or cartridge assembly 200.

Figure 11C:
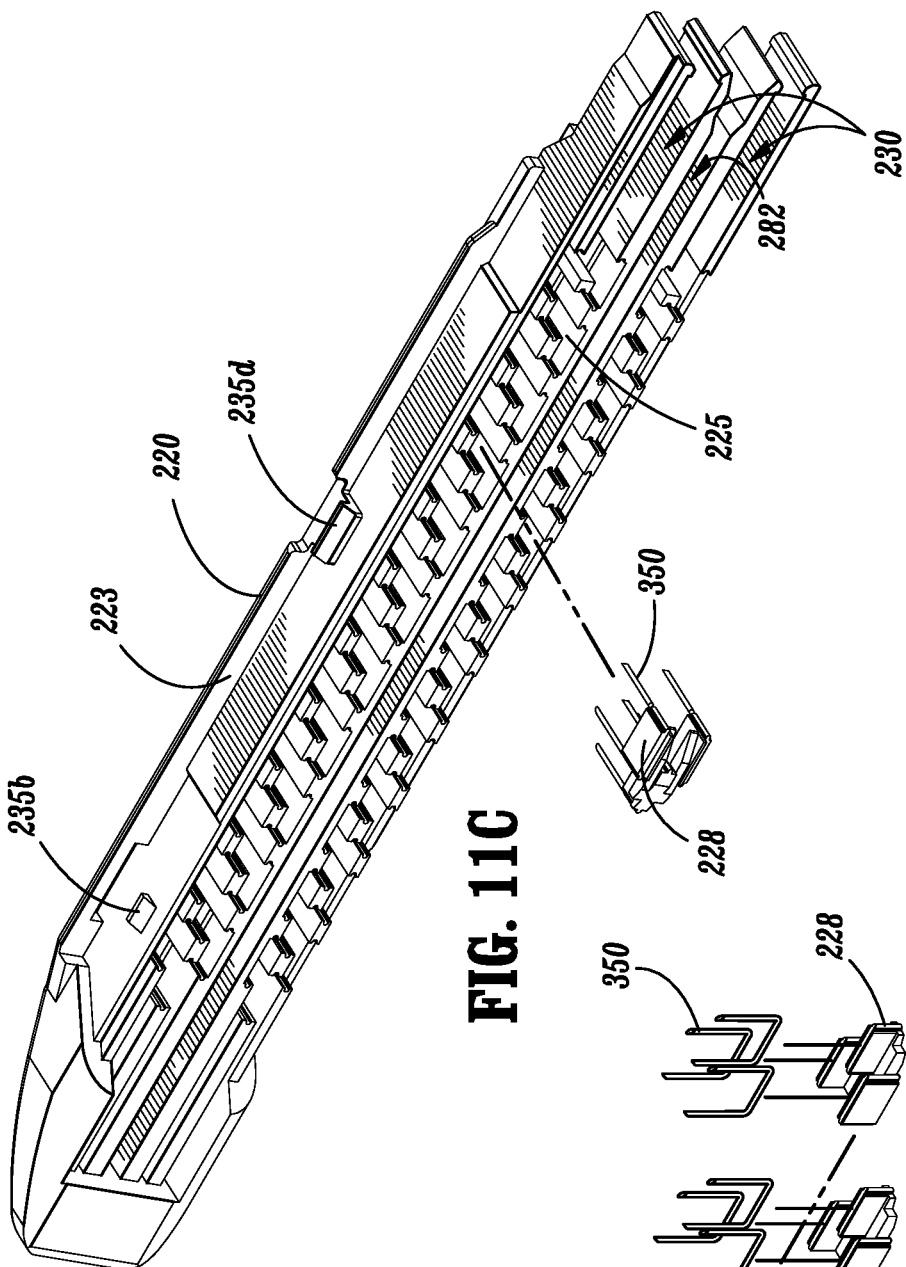
FIG. 11C is a bottom perspective view with parts separated of the cartridge assembly of FIG. 11A.
Figure 11D:
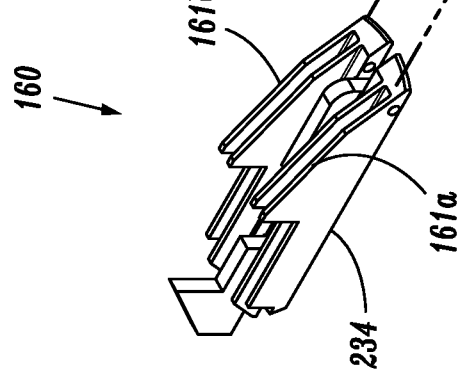
FIG. 11D shows an enlarged view of the cooperative relationship between the sled, the surgical fasteners and a plurality of staple pushers which form part of the staple cartridge of FIGS. 11A-11C.

As best shown in FIGS. 6A, 6B, 11A and 11B, channel assembly 120 is dimensioned to house staple cartridge assembly 200 therein. More particularly, channel assembly 120 includes a bottom surface 128 having upwardly extending side walls or flanges 121*a* and 121*b* which define elongated support channel 125 which, in turn, is dimensioned to mountingly receive staple cartridge assembly 200 therein. Channel assembly 120 also includes a plurality of mechanical interfaces, here apertures 127*a*, 127*b*, 127*c* and 127*d*, which matingly receive a corresponding plurality of mechanical interfaces, here, protrusions 235*a*, 235*b*, 235*c* and 235*d*, disposed in the outer-facing surfaces of staple cartridge assembly 200 (FIGS. 2 and 11C).

Staple cartridge assembly 200 can be assembled and mounted within channel assembly 120 during the manufacturing or assembly process and sold as part of overall tool assembly 100, or staple cartridge assembly 200 may be designed for selective mounting to channel assembly 120 as needed and sold separately, e.g., as a single use replacement, replaceable or disposable staple cartridge assembly 200. Preferably, staple cartridge assembly 200 is manufactured to include sled 160 and dynamic clamping member 150. Alternatively and as discussed below with respect to FIG. 15, dynamic clamping member 150 with a knife may be sold as part of the replaceable staple cartridge assembly 200 without a knife blade 155*a* (but preferably with a knife blade 155*a* to enhance and/or insure accurate cutting of tissue 400 after staple deformation. Tool assembly 100 may also be sold as a kit that includes a variety of staple cartridges 200 containing surgical fasteners 500 of different sizes, and/or arranged to be ejected in different patterns, any of which may be selectively-coupled to the channel assembly 120 as desired for use during a particular operation.

The proximal end of each upwardly extending flange 121*a* and 121*b* of the channel assembly 120 includes the aforementioned cul de sacs 123*a*, 123*b* which allow pins 119*a* and 119*b* of anvil assembly 110 to pivot therein, and apertures 122*a* and 122*b* which are dimensioned to receive pivot pin 59. When assembled, pivot pin 59 also passes through apertures 53*a*, 53*b* of pivot block 50 along the "Y" axis. Rotation of the pivot block 50 about the "Y" axis correspondingly rotates tool assembly 100 about the "Y" axis. Rotation of pivot block 50 about pin 57 along "Z" axis rotates tool assembly 100 about the "Z" axis.

Figure 6B:
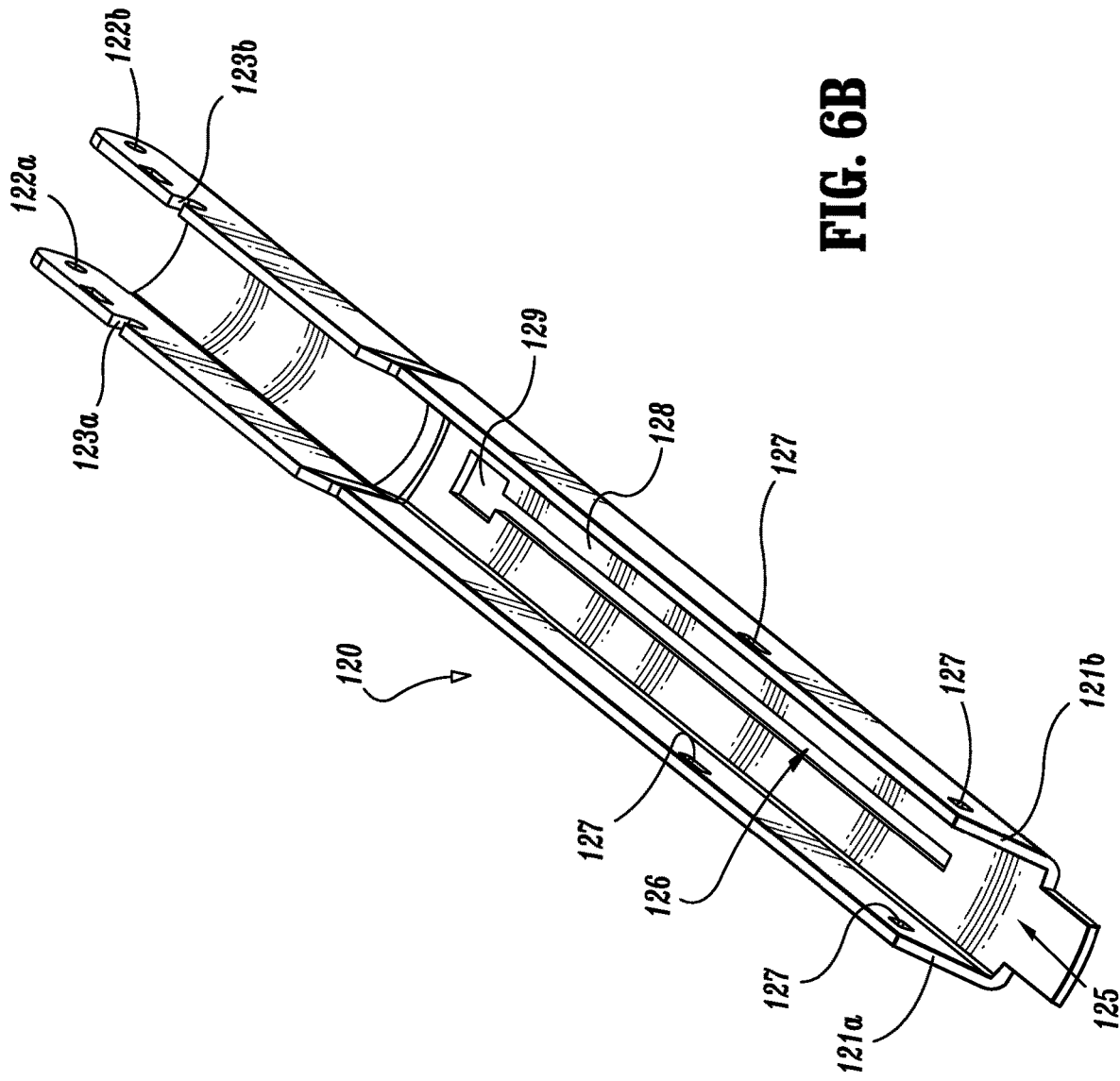
FIG. 6B is a top, perspective view of the channel assembly of FIG. 6A.
Figure 7A:
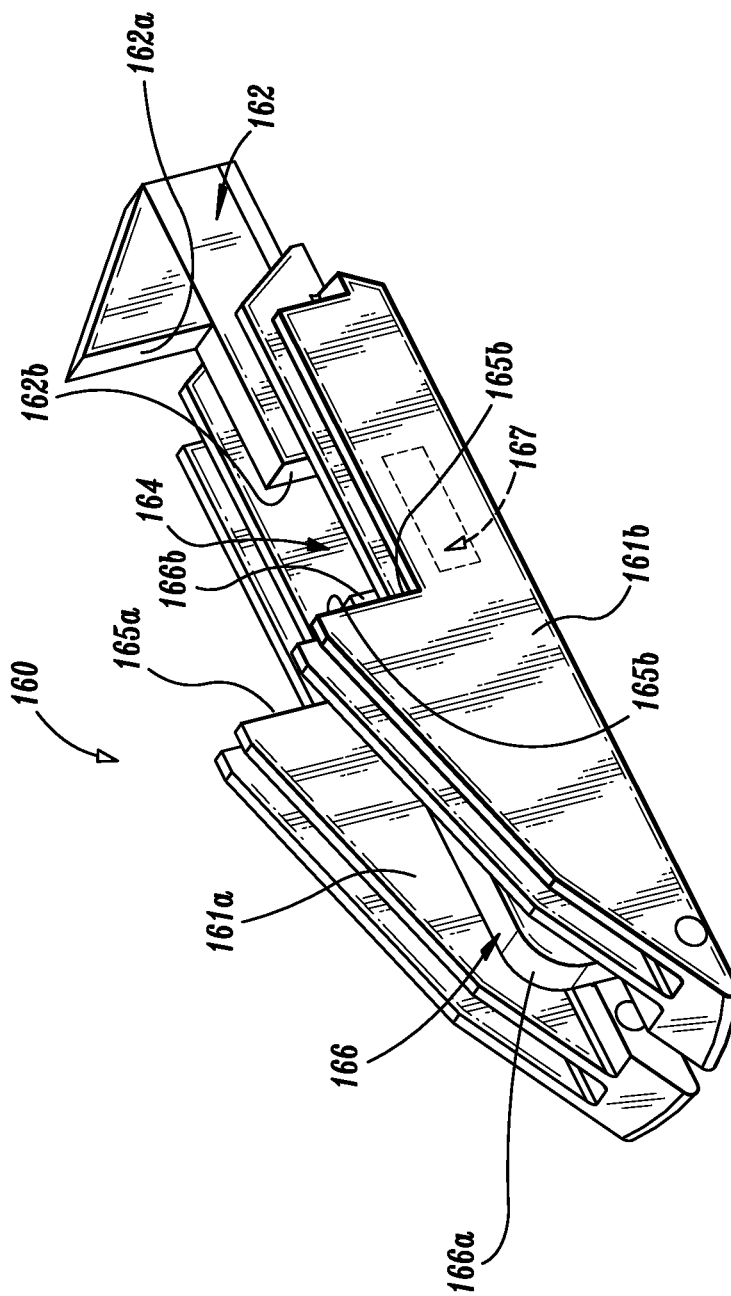
FIG. 7A is a side, perspective view of a sled for supporting the dynamic clamping member according to the present disclosure.
Figure 7B:
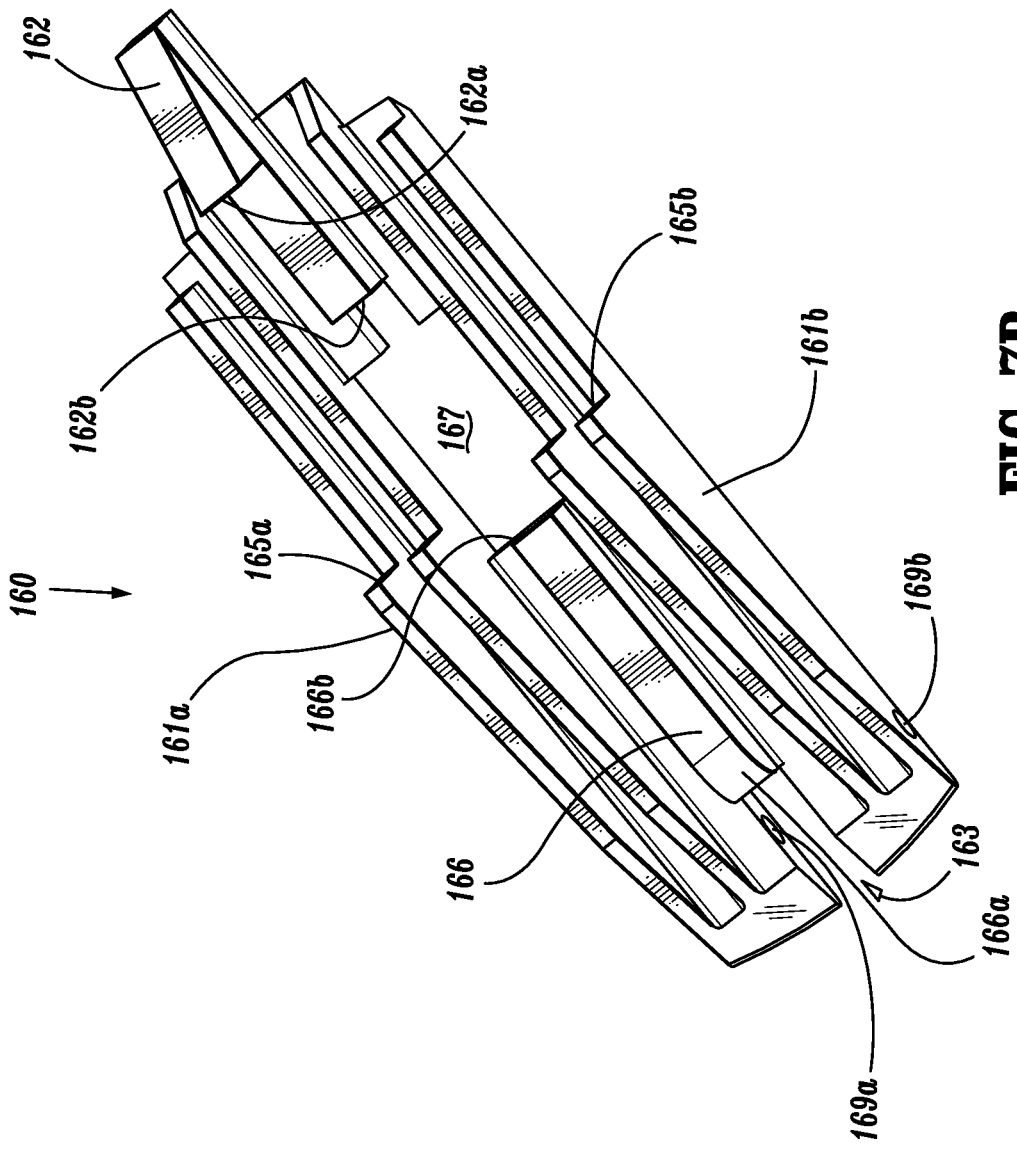
FIG. 7B is a top, perspective view of the sled of FIG. 7A.
Figure 7C:
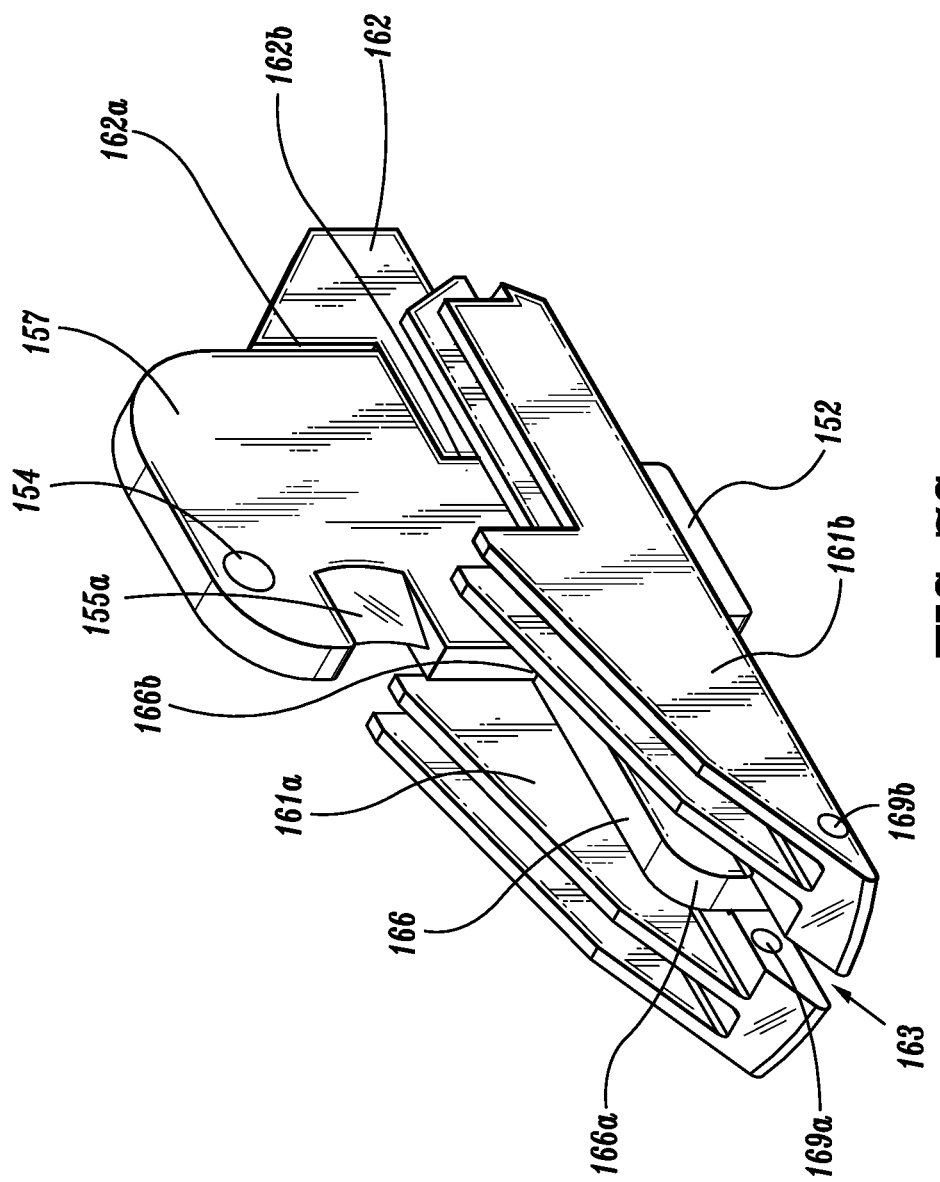
FIG. 7C is a perspective view showing the dynamic clamping member disposed within the sled.

As best shown in FIG. 6B, bottom surface 128 of channel assembly 120 also includes an elongated longitudinal slot 126 which includes and communicates at its proximal end with a cut out or notch 129. Notch 129 is dimensioned to allow bottom flange 152 of dynamic clamping member 150 to pass therethrough. The narrower portion of slot 126 is dimensioned to slidingly receive and allow upward support or extension 151 to pass therethrough. More particularly and as also shown in FIGS. 7A and 7B, bottom flange 152 of dynamic clamping member 150 is passed through opening or channel 164 through cut out or notch 167 in the base of sled 160, and through notch 129 in bottom wall 128 of channel assembly 120. When bottom flange 152 of dynamic clamping member 150 is extended below the surface of bottom wall 128 of channel 120, dynamic clamping member 150 is moved distally so that bottom flange 152 slidingly engages the underside of bottom wall 128 adjacent slot 126 and upward extension 151 engages in channel 164. As can be appreciated, this slidingly locks bottom flange 152 of the dynamic damping member 150 and sled 160 within the channel assembly 120.

Bottom flange 152 of dynamic damping member 150 in cooperation with the pin 159 and slot 112 arrangement of dynamic damping member 150 and anvil assembly 110, slidingly secure the dynamic clamping member 150 within opposing slots 126 and 112 and prevents unintentional displacement of anvil assembly 110 relative to staple cartridge assembly 200 (either vertically ("Z" axis") or transversely ("Y" axis)) during the clamping, fastening and severing procedures. As mentioned above, the heavy gauge material of the anvil assembly 110 also reduces unintentional displacement of the dynamic damping member 150 during distal translation thereof. Thus, in addition to severing tissue 400, dynamic damping member 150 of the present disclosure also acts to oppose the forces associated with compression of tissue, deformation of the surgical fasteners 500 and severing of tissue 400.

As mentioned above, bottom surface 128 of channel assembly 120 acts as a carrier to define elongated support channel 125 for receiving the staple cartridge assembly 200. With respect to the staple cartridge assembly 200, corresponding tabs 235a, 235b, 235c, 235d formed along staple cartridge assembly 200 and elongated support channel 125 function to retain staple cartridge assembly 200 within support channel 125 (See FIG. 11C). Staple cartridge assembly 200 also includes offset retention slots 225 for receiving a plurality of fasteners 500 and staple pushers 228 therein. A series of spaced-apart longitudinal slots 230 extend through staple cartridge assembly 200 to accommodate a pair of upwardly extending, bifurcated cam wedges 161a, 161b of sled 160. As best shown in FIG. 11A, a centrally-located, longitudinal slot 282 extends substantially along the length of staple cartridge assembly 200 to facilitate passage of upward extension 151 of dynamic damping member 150 therethrough. When deformed using the embodiment shown, the surgical fasteners 500 form two sets of three staple rows 232a and 232b, one set to each side of slot 282.

When tool member 100 is assembled, sled 160 is slidingly positioned between the staple cartridge assembly 200 and the channel assembly 120 (See FIG. 3). Sled 160 and the inner-working components of staple cartridge assembly 200 detailed above operatively cooperate to deform staples 500. More particularly, sled 160 includes upwardly extending, bifurcated cam wedges 161 a and 161 b which engage and cooperate with a series of staple pushers 228 to drive staples 350 through slots 225 from cartridge assembly 200 and deform against staple forming pockets 11 of anvil assembly 100.

During operation of the surgical stapler 10, sled 160 translates preferably distally through longitudinal slots 230 of staple cartridge assembly 200 to advance cam wedges 161 a and 161 b into sequential contact with pushers 228, to cam and cause pushers 228 to translate vertically within retention slots 225 and urge fasteners 500 from retention slots 225 against fastener forming pockets 111 in bottom facing surface 114b of anvil assembly 110 (See FIG. 4). One such type of staple forming pocket or cavity 111 is shown and described in commonly owned U.S. Pat. No. 6,330,965 the entire contents of which are hereby incorporated by reference herein.

As mentioned above, dynamic clamping member 150 is mounted on and preferably rides atop, on or in sled 160 (FIGS. 7A and 7B). In the embodiment shown, when assembled, the lower portion of upward extension 151 of dynamic clamping member 150 is generally positioned in slot 164 defined in sled 160 axially between the proximally facing edge 166a of spacer 166 and the distally facing edge 162b and upwardly extending proximal edge 162a of a rear flange 162.

Dynamic clamping member 150 is secured to sled 160 through a slot 167 that extends through the base of sled 160. More particularly, the base of upward extension 151 of dynamic clamping member 150 is securely disposed with the second slot 167 which extends through the bottom of sled 160 and is defined by proximally facing or trailing edge 166b of a spacer 166 and the distal edge 162b of flange 162. Specifically, the leading edge 153a (FIG. 10) of upper extension 151 abuts against the trailing edge of spacer 166b and the trailing edge 153b (FIG. 10) of upper extension 151 abuts against distal edge 162b of flange 162 to axially secure dynamic clamping member 150 to and axially in sled 160.

Leading edge 166a of the spacer 166 rides within and along slot 282 of staple cartridge assembly 200 to positively guide the sled 160 along an ideal stapling and cutting path preferably centrally and axially through the tissue 400. Thus, upon distal movement of sled 160 to eject surgical fasteners 500, dynamic clamping member 150, securely disposed within sled 160, travels along slot 282 of staple cartridge assembly 200 and sequentially severs tissue 400 between the two rows 232a and 232b of formed fasteners 500 (See FIG. 11A). As explained in more detail below with respect to FIGS. 12 and 13, the distal end of sled 160 may includes apertures 169a and 169b to receive a suitable elongated flexible member, e.g., a cable 900, which upon movement thereof advances sled 160 to form surgical fasteners 500 and sever tissue 400.

Figure 10:
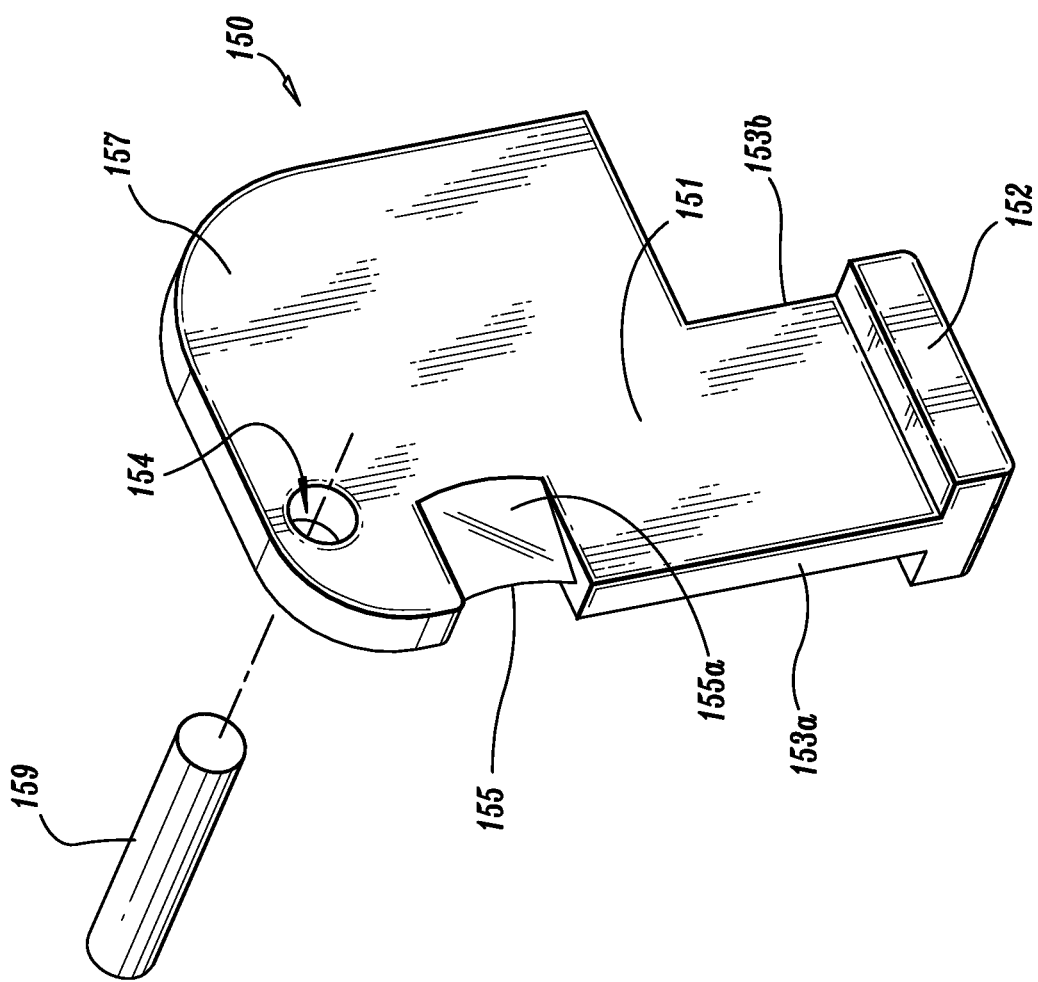
FIG. 10 is a side, perspective view of the dynamic clamping member according to the present disclosure.

As best shown in FIG. 10, dynamic clamping member 150 includes an upper portion 157 having a transverse aperture 154 with a pin 159 mountable or mounted therein, a central support or upward extension 151 and substantially T-shaped bottom flange 152 which, as described above, mutually cooperate to slidingly retain dynamic clamping member 150 along an ideal cutting path during longitudinal, distal movement of sled 160. The leading cutting edge 155, here, knife blade 155a, is dimensioned to ride within slot 282 of staple cartridge assembly 200 and separate tissue 400 once stapled. It is envisioned that leading edge 155 of the dynamic clamping member 150 may be serrated, beveled or notched to facilitate tissue cutting. More particularly, it is contemplated that the combination of the enhanced closure force as a result of the heavy gauge material of the anvil assembly 110 together with the above described uniquely designed or positioned dynamic clamping member 150 (or dynamic clamping member 150" of FIG. 14) permits accurate cutting of tissue 400 when leading edge 155 is advanced through tissue 400. It is also understood that the upper camming member need not be a pin but can be any integral or removable suitable outwardly protruding cam surface(s). The same applies to bottom flange 152 which can be any suitable camming surface, including a pin or a removable pin, a button to facilitate mounting of the dynamic clamping member into the sled 160 or channel assembly 120.

It is also envisioned that the strength of the over and under camming configuration of dynamic clamping member 150 in combination with the increased strength of anvil assembly 110 (i.e., made from a heavy gauge surgical stainless steel) also prevents dynamic damping member 150 from cutting vertically offline or buckling and eliminates the need to cantilever dynamic clamping member 150 as it moves through tissue 400. In other words, by preferably utilizing a heavy gauge material for the anvil assembly 110 (and possibly the channel assembly 120) and utilizing substantially aligned upper and lower slidingly engaging surfaces of the dynamic clamping member 150 (here, pin 159 and bottom flange 152) to ride between the anvil assembly 110 and the channel assembly 120 in substantial vertical registration, the normal forces associated with stapling and cutting tissue 400 are sufficiently opposed thus maintaining a consistent maximum and substantially uniform gap in the stapling and cutting area between the opposing tissue contacting surfaces (i.e., staple cartridge surface 231 and bottom anvil surface 114b) during the stapling and cutting processes. Moreover, the provision of the heavy gauge material for the anvil assembly 110 and the arrangement of the pin 159 and bottom flange 152 also operate to further proximate or further clamp the tissue at a point distal to the dynamic damping member 150 which forces fluid from the tissue 400 to further enhance the stapling and cutting processes. It is envisioned that alternative upper and lower sliding camming surfaces may be employed to accomplish a similar purpose, e.g., plates, rails, ball bearing etc.

From the foregoing and with reference to the various figure drawings, those skilled in the art will appreciate that certain modifications can also be made to the present disclosure without departing from the scope of the present disclosure. For example, the above-described tool assembly 100 may be part of or incorporated into a disposable loading unit (DLU) such as disclosed in U.S. Pat. No. 6,330,965 or attached directly to the distal end of any known surgical stapling device. A handle assembly for actuating the approximation member(s) can be selected from a variety of actuating mechanisms including toggles, rotatable and slideable knobs, pivotable levers or triggers, and any combination thereof. The use of the above-described tool assembly 100 as part of a robotic system is also envisioned.

It is also envisioned that many different actuators may be employed to advance the sled 160 through the tissue 400. For example, it is envisioned that the tool assembly 100 (or one of the sub-assemblies associated therewith, i.e., channel assembly 120 or staple cartridge assembly 200 or anvil assembly 110) may include one or more pulleys to advance the sled 160 through the tissue 400 to staple and cut the same.

Figure 12A:
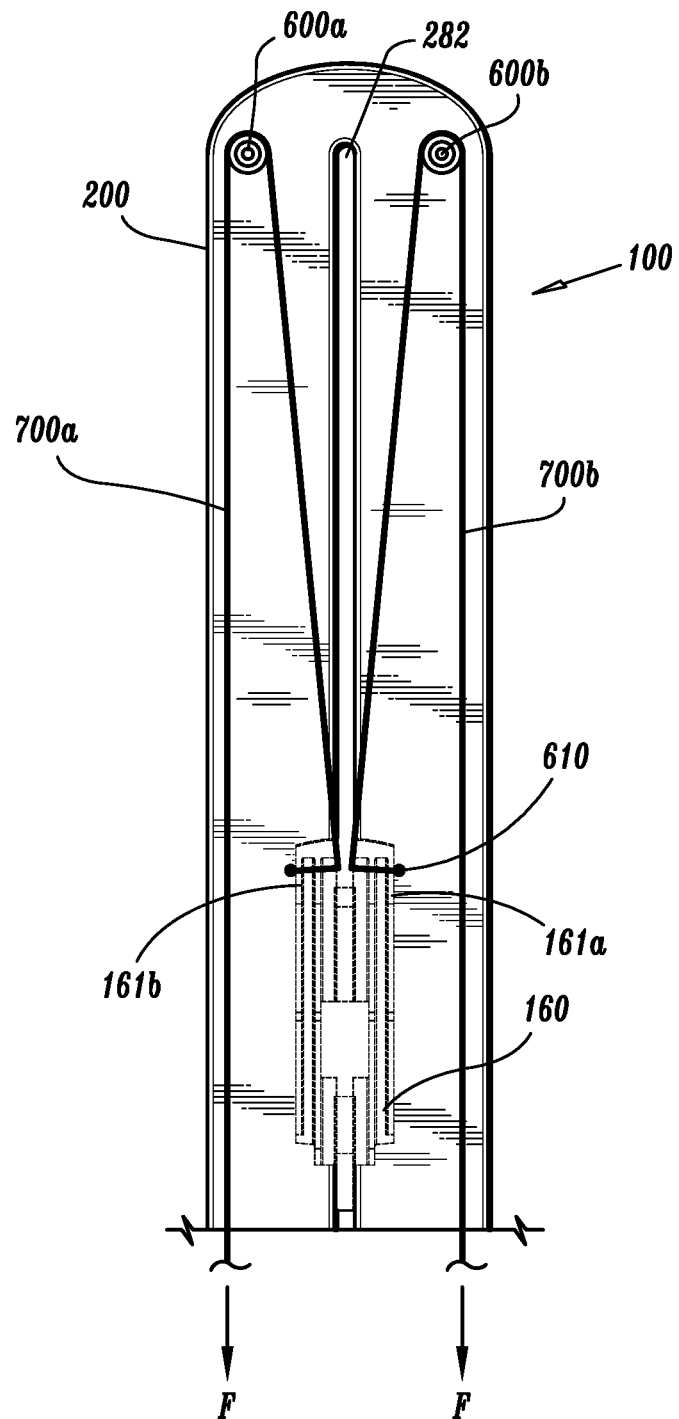
FIG. 12A is a schematic illustration of a pulley-like drive system for advancing the sled through the tissue, including a pair of belts.
Figure 12B:
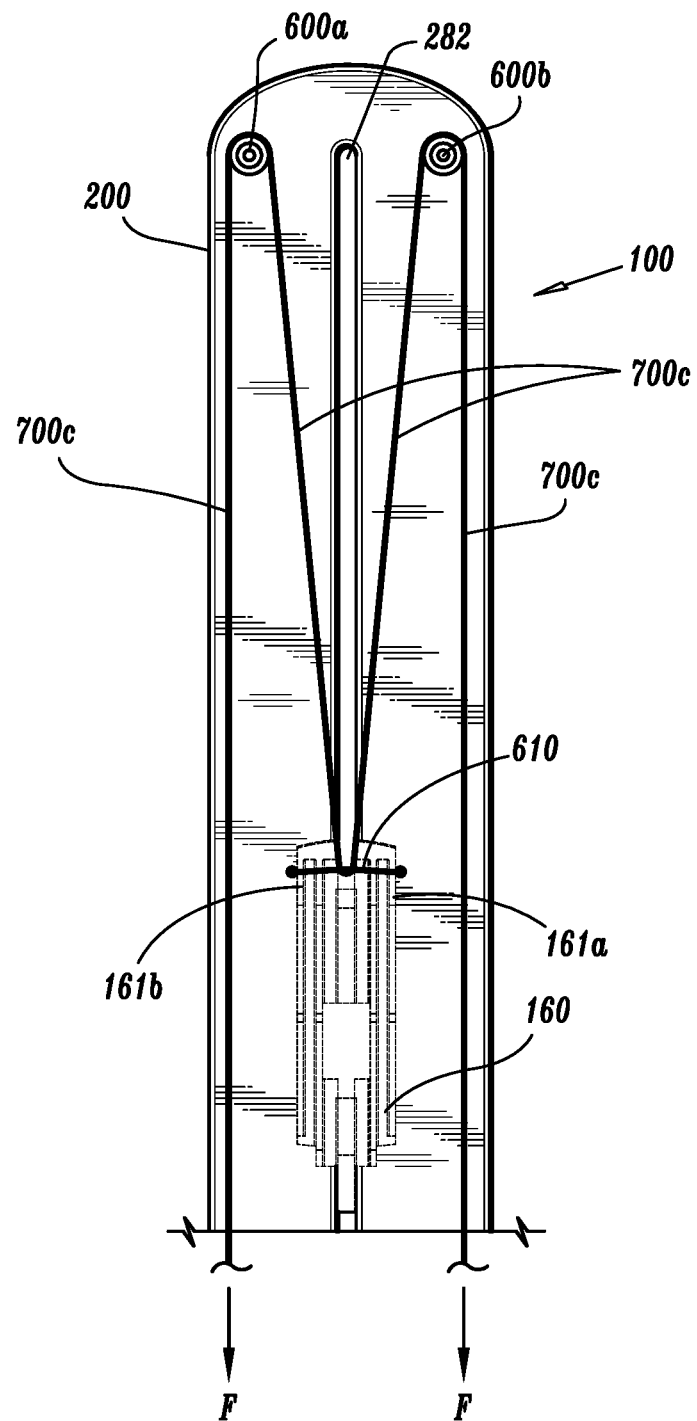
FIG. 12B is a schematic illustration of a pulley-like drive system for advancing the sled through the tissue, including a single belt.

For example, as shown in FIG. 12A, a pair of cables, ropes, threads or bands or belts 700a, 700b may be fed distally through cartridge assembly 200 or channel assembly 120 through or around respective pins, capstans, or pulleys 600a, 600b, and pass proximally toward and attach to sled 160. Alternatively and as shown in FIG. 12B, a single belt can replace belts 700a and 700b and can be passed through apertures 169a and 169b at the distal end of sled 160, or passed into a gap 163 and around behind a pin 610 which is mounted through apertures 169a and 169b.

One or more pins 610 may be disposed within sled 160 such that a proximal force "F" on the corresponding bands 700a and 700b advances the sled 160 distally to eject and form staples 500 against anvil assembly 110 and cut tissue 400. It is envisioned that the band or belts may be made from a high strength material sold under the trademark Kevlar®, or other man-made fibers or materials available for generalized use in the industrial arts and suitable for this intended surgical use. As can be appreciated, utilizing a dual pin or pulley system as schematically shown in FIG. 12 maintains the balance of the proximally-actuated forces "F" on either side of staple cartridge assembly 200 as sled 160 moves through tissue 400. As also can be appreciated, this assures uniform and consistent stapling and cutting of tissue 400 by dynamic clamping member 150.

Figure 13:
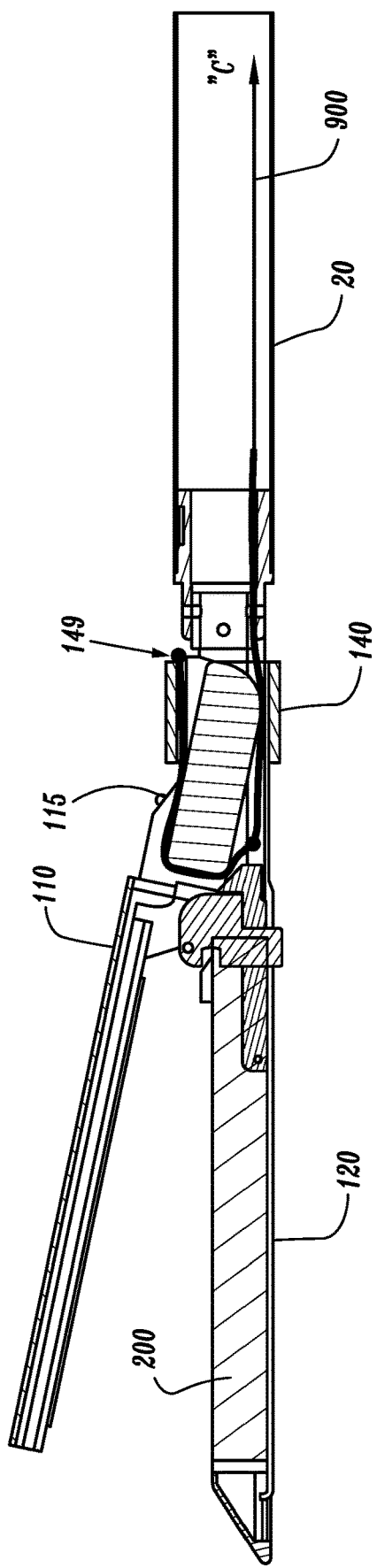
FIG. 13 is a side cross sectional schematic view showing one possible actuating mechanism for actuating a clamp to compress and cut tissue.

FIG. 13 shows one possible suitable actuating system to actuate pre-clamping collar 140 to force anvil assembly 110 to close relative to staple cartridge assembly 200. More particularly, a cable 900 may be utilized to move pre-clamping collar 140 distally onto and over cam surface 115 to close the anvil 110 relative to the staple cartridge assembly 200 and compress the tissue 400. Preferably, cable 900 attaches to the pre-clamping collar 140 at or near point 149 and is fed through a passageway in anvil assembly 110 (or under a proximal portion of anvil assembly 110) and fed proximally through shaft 20. Actuating of cable 900 in the direction "C" forces pre-damping collar 140 distally against cam surface 115 to close anvil assembly 110 relative to staple cartridge assembly 200. A return mechanism, e.g., a spring, cable system or the like (not shown), may be employed to return pre-clamping collar 140 to a pre-clamping orientation which re-opens anvil assembly 110.

FIG. 14 shows an alternate embodiment of a dynamic damping collar 150" which includes an upper portion 157" having a transverse aperture 154 within which pin 159 is mountable or mounted therein, upward extension 151 and substantially T-shaped bottom flange 152" which, as similarly described above with respect to FIG. 10, mutually cooperate to slidingly retain dynamic damping member 150" along an ideal cutting path during longitudinal, distal movement of sled 160. The leading cutting edge 155" of knife blade 155a" is dimensioned to ride within slot 282 of staple cartridge assembly 200 and separate tissue 400 once stapled.

It is envisioned that the combination of the enhanced closure force as a result of the heavy gauge material of the anvil assembly 110 together with uniquely designed dynamic clamping member 150" permits accurate cutting of tissue 400 when leading edge 155" is advanced through tissue 400. It is also contemplated that the strength of the over and under camming configuration of dynamic clamping member 150" in combination with the increased strength of anvil assembly 110 (i.e., made from a heavy gauge surgical stainless steel) also prevents dynamic damping member 150" from cutting vertically offline or buckling and eliminates the need to cantilever dynamic clamping member 150" as it moves through tissue 400. In other words, by preferably utilizing a heavy gauge material for the anvil assembly 110 substantially aligning upper and lower slidingly engaging surfaces in vertical registration, dynamic clamping member 150" rides between the anvil assembly 110 and the channel assembly 120 in substantial vertical registration and the forces associated with stapling and cutting tissue 400 are sufficiently opposed thus maintaining a consistent maximum and substantially uniform gap in the stapling and cutting area between the opposing tissue contacting surfaces 231 and 114b during the stapling and cutting processes.

The dynamic clamping member 150, 150" of this disclosure is an improvement over known clamping members. Since the upper and lower camming surfaces are substantially opposed, i.e., substantially vertically aligned, the forces to which it is subjected during its operation are substantially only tensile forces. Consequently, the design of the dynamic clamping member 150 renders it significantly strong and significantly resistant to buckling. Accordingly, the cutting edge 155 is unlikely to buckle. Further, since the cutting edge 155 for cutting tissue is also substantially aligned with the upper and lower camming surfaces 159 and 152, the closing force of the dynamic damping member 150 is imparted closer to and preferably more aligned with the cutting edge. This enhances the cutting action of the cutting edge.

The preferred use of a damping collar 140 to pre-damp, i.e., initially approximate the anvil assembly 110 and cartridge assembly 200, in combination with the use of a dynamic clamping member 150 to subsequently clamp, preferably further damp, i.e., further proximate, the anvil 110 and cartridge 200 assemblies, provides several advantages. It enhances tissue stabilization and compression. During pre-clamping and approximation, clamping collar 140 squeezes, i.e., pre-squeezes tissue, between and distally along the respective tissue contracting or facing surfaces of the anvil assembly 110 and cartridge assembly 120. During subsequent, preferably further clamping and approximation with the dynamic damping member 150, there is believed to be less fluid and fluid flow in the tissue in the area of further damping. This enhances obtaining a uniform tissue gap and better staple formation along the tool assembly 100. With less fluid flow in the area of and during stapling, staple legs more accurately hit their staple pockets 111 in the anvil 110 forming surface. The advantages pre-damping and subsequent clamping are further enhanced by use of stronger heavier gauge anvil assembly 110, for example because there is less of a tendency for distal end of anvil assembly 110 to bow outwardly away from cartridge assembly 200. Also, the squeezing effect on the tissue during pre-clamping and clamping is more pronounced, increasingly so from the mid to distal end of the anvil assembly 110. Consequently, tissue fluid is forced further distally out to and past the distal end of the anvil assembly 110 and tool assembly 100. This reduces fluid flow in the area of and during stapling with the dynamic damping member 150. In addition to the benefits explained above, this reduces the need to cantilever the camming force out ahead of the clamping member 150, and allows the upper camming surface here, pin 159, to be effectively disposed in substantially vertical alignment meaning at least some portion of the upper and lower camming surfaces 159, 152 are vertically aligned. Thus, the most preferred arrangement and procedure is to have a clamping collar 140 for pre-clamping, a dynamic clamping member 150 for further clamping, and each being effected on a strong, or, preferably, very strong anvil assembly 110.

The present disclosure also relates to a method of stapling tissue and includes the steps of providing a stapler having a tool assembly at a distal end thereof, the tool assembly including a channel assembly for supporting a staple cartridge which carries a plurality of staples and an anvil dimensioned having, e.g., shaped pockets to deform the plurality of staples ejected from the staple cartridge thereagainst. The tool assembly also includes a sled which is movable from a first position to a subsequent position to force the plurality of staples from the staple cartridge through tissue and against the anvil, and a dynamic clamping member which moves with the sled. The dynamic damping member includes a first mechanical interface which slidingly engages the anvil and a second mechanical interface which slidingly engages the channel assembly. The first and second mechanical interfaces of the dynamic clamping member are in substantial vertical registration relative to one another to oppose the expansive forces associated with clamping, stapling, and if a knife is engaged on the dynamic clamping member, cutting tissue.

The method according to the present invention also includes the steps of: approximating and grasping tissue between the opposing surfaces of the anvil and the staple cartridge; clamping the anvil and staple cartridge in position about the tissue; and firing the stapler to advance the sled and the dynamic clamping member distally to eject the staples from the staple cartridge to deform against the anvil to fasten the tissue and to subsequently cut the tissue along a predetermined cutting path. The firing step can employ the substantially over and under dynamic clamping member to further proximate the opposing surfaces of the anvil assembly and the staple cartridge at progressively moving points which are distal to the knife during translation of the dynamic damping member.

Although the subject surgical stapler and various assemblies associated therewith have been described with respect to preferred embodiments, it will be readily apparent to those having ordinary skill in the art to which it appertains that changes and modifications may be made thereto without departing from the spirit or scope of the subject devices. While several embodiments of the disclosure have been shown in the drawings and described herein, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A surgical tool for performing robotic surgery, the surgical tool comprising:
   a shaft having a proximal end and a distal end, the proximal end being removably associated with a robotic system; and
   a tool assembly attached to the distal end of the shaft, the tool assembly comprising:
   a clamping member, the clamping member comprising:
      a lower transverse member comprising first and second transverse protrusions extending in substantially opposite directions along a first axis, each of the first and second transverse protrusions having an upper engagement surface,
      an upper transverse member comprising third and fourth transverse protrusions extending in substantially opposite directions along a second axis, the second axis being substantially parallel to the first axis, and
      an upward extension extending between and connecting the lower transverse member and the upper transverse member along a third axis substantially perpendicular to the first and second axes, the upper transverse member and the lower transverse member being substantially transverse to the upward extension,
   a first jaw comprising:
      a proximal end,
      a distal end,
      the first jaw having a support channel between the proximal end of the first jaw and the distal end of the first jaw, the support channel being configured to receive a staple cartridge assembly, the staple cartridge assembly having at least one tab, a longitudinal slot, at least three rows of staples disposed on each side of the longitudinal slot, and a sled including at least one cam wedge, the at least three rows of staples on each side of the longitudinal slot being substantially parallel to the longitudinal slot, the first jaw further comprising at least one aperture along an edge of the first jaw, and the at least one tab of the staple cartridge assembly being engageable with the at least one aperture of the first jaw, at least the at least one aperture and the at least one tab being configured to cooperate to removably and replaceably retain the staple cartridge assembly within the support channel to permit replacement of the staple cartridge assembly during a surgical procedure, and
      a surface of the first jaw having a longitudinal slot between the proximal end of the first jaw and the distal end of the first jaw, the surface of the first jaw being configured to engage with the upper engagement surfaces of the first and second transverse protrusions of the lower transverse member of the clamping member as the upward extension travels through the longitudinal slot such that the first and second transverse protrusions slide along the surface of the first jaw,
a second jaw pivotable relative to the first jaw, the second jaw comprising:
a proximal end,
a distal end,
an anvil having at least one anvil surface, the at least one anvil surface having at least one staple forming pocket, and
the anvil defining an elongated slot between the proximal end of the second jaw and the distal end of the second jaw, the elongated slot being configured to receive the third and fourth transverse protrusions of the upper transverse member of the clamping member as the upward extension travels through the elongated slot, wherein movement of the clamping member along the first and second jaws such that the upper engagement surfaces of the first and second transverse protrusions of the lower transverse member of the clamping member move along the surface of the first jaw and the third and fourth transverse protrusions of the upper transverse member of the clamping member move through the elongated slot and causes at least one of:
the first and second jaws to clamp, and
staples to be ejected from a staple cartridge assembly when a staple cartridge assembly is received within the support channel of the first jaw.

2. The surgical tool of claim 1, wherein the first jaw further includes a staple cartridge assembly received within the support channel of the first jaw, the staple cartridge assembly defining a longitudinal slot, and having at least one tab at least three rows of staples disposed on each side of the longitudinal slot, and a sled including at least one cam wedge, the at least three rows of staples on each side of the longitudinal slot being substantially parallel to the longitudinal slot, and the at least one tab of the staple cartridge assembly being engageable with the at least one aperture of the first jaw, at least the at least one aperture and the at least one tab cooperating to removably and replaceably retain the staple cartridge assembly within the support channel to permit replacement of the staple cartridge assembly during a surgical procedure.

3. The surgical tool of claim 2, wherein the movement of the upper engagement surfaces of the first and second transverse protrusions of the lower transverse member of the clamping member along the surface of the first jaw and movement of the third and fourth transverse protrusions of the upper transverse member of the clamping member through the elongated slot further causes:
the sled to ride distal to the clamping member along the support channel, and
the at least one cam wedge to cooperate with at least one staple pusher of the staple cartridge assembly to eject at least one of the staples from the staple cartridge assembly.

4. The surgical tool of claim 2, wherein the sled comprises at least two cam wedges.

5. The surgical tool of claim 1, further comprising the tool assembly being connected to the distal end of the shaft by a connection mechanism comprising:
a first pivot axis being substantially perpendicular to a longitudinal axis of the shaft, wherein the tool assembly is pivotable about the first pivot axis with respect to the shaft, and
a second pivot axis being substantially perpendicular to the first pivot axis, wherein the tool assembly is pivotable about the second pivot axis with respect to the shaft.

6. The surgical tool of claim 1, wherein the clamping member is configured without a knife blade.

7. The surgical tool of claim 6, wherein the tool assembly is rotatable about the longitudinal axis of the shaft.

8. A surgical tool for performing robotic surgery, the surgical tool comprising:
a shaft having a proximal end and a distal end, the proximal end being removably associated with a robotic system;
a tool assembly comprising:
a clamping member, the clamping member comprising:
a lower transverse member comprising first and second transverse protrusions extending in substantially opposite directions along a first axis, each of the first and second transverse protrusions having an upper engagement surface,
an upper transverse member comprising third and fourth transverse protrusions extending in substantially opposite directions along a second axis substantially parallel to the first axis, and
an upward extension extending between and connecting the lower transverse member and the upper transverse member along a third axis substantially perpendicular to the first and second axes, the upper transverse member and the lower transverse member being substantially transverse to the upward extension,
a first jaw comprising:
a proximal end,
a distal end,
the first jaw having a support channel between the proximal end of the first jaw and the distal end of the first jaw, the support channel being configured to receive a staple cartridge assembly, the staple cartridge assembly having at least one tab, a longitudinal slot, at least three rows of staples disposed on each side of the longitudinal slot, and a sled including at least one cam wedge, the at least three rows of staples on each side of the longitudinal slot being substantially parallel to the longitudinal slot, the first jaw further comprising at least one aperture along an edge of the first jaw, and the at least one tab of the staple cartridge assembly being engageable with the at least one aperture of the first jaw, at least the at least one aperture and the at least one tab being configured to cooperate to removably and replaceably retain the staple cartridge assembly within the support channel to permit replacement of the staple cartridge assembly during a surgical procedure, and
a surface of the first jaw having a longitudinal slot between the proximal end of the first jaw and the distal end of the first jaw, the surface of the first jaw being configured to engage with the upper engagement surfaces of the first and second transverse protrusions of the lower transverse member of the clamping member as the upward extension travels through the longitudinal slot such that the first and second transverse protrusions slide along the surface of the first jaw, and a second jaw pivotable relative to the first jaw, the second jaw comprising:

a proximal end,
a distal end,
an anvil having at least one anvil surface, the at least one anvil surface having at least one staple forming pocket, and
the anvil having an elongated slot between the proximal end of the second jaw and the distal end of the second jaw, the elongated slot being configured to receive the third and fourth transverse protrusions of the upper transverse member of the clamping member as the upward extension travels through the elongated slot,
wherein movement of the clamping member along the first and second jaws causes movement of the upper engagement surfaces of the first and second transverse protrusions of the lower transverse member of the clamping member along the surface of the first jaw and movement of the third and fourth transverse protrusions of the upper transverse member of the clamping member through the elongated slot causes at least one of:
the first and second jaws to clamp, and
staples to be ejected from the staple cartridge assembly when a staple cartridge assembly is received within the support channel of the first jaw, and
a connection mechanism connecting the tool assembly to the shaft, the connection mechanism comprising:
a first pivot axis being substantially perpendicular to a longitudinal axis of the shaft, wherein the tool assembly is pivotable about the first pivot axis with respect to the shaft, and
a second pivot axis being substantially perpendicular to the first pivot axis, wherein the tool assembly is pivotable about the second pivot axis with respect to the shaft.

9. The surgical tool of claim 8, wherein the first jaw further includes a staple cartridge assembly received within the support channel of the first jaw, the staple cartridge assembly defining a longitudinal slot, and having at least one tab at least three rows of staples disposed on each side of the longitudinal slot, and a sled including at least one cam wedge, the at least three rows of staples on each side of the longitudinal slot being substantially parallel to the longitudinal slot, and the at least one tab of the staple cartridge assembly being engageable with the at least one aperture of the first jaw, at least the at least one aperture and the at least one tab cooperating to removably and replaceably retain the staple cartridge assembly within the support channel to permit replacement of the staple cartridge assembly during a surgical procedure.

10. The surgical tool of claim 9, wherein the tool assembly is rotatable about the longitudinal axis of the shaft.

11. The surgical tool of claim 9, wherein the movement of the upper engagement surfaces of the first and second transverse protrusions of the lower transverse member of the clamping member along the surface of the first jaw and movement of the third and fourth transverse protrusions of the upper transverse member of the clamping member through the elongated slot further causes:
the sled to ride distal to the clamping member along the support channel, and
the at least one cam wedge to cooperate with at least one staple pusher of the staple cartridge assembly to eject at least one of the staples from the staple cartridge assembly.

12. The surgical tool of claim 11, the clamping member being configured to ride within the sled, wherein the movement of the upper engagement surfaces of the first and second transverse protrusions of the lower transverse member of the clamping member along the surface of the first jaw and movement of the third and fourth transverse protrusions of the upper transverse member of the clamping member through the elongated slot further causes:
the sled to ride along the support channel, and
the at least one cam wedge to cooperate with at least one staple pusher of the staple cartridge assembly to eject at least one of the staples from the staple cartridge assembly.

13. The surgical tool of claim 9, wherein the sled comprises at least two cam wedges.

14. The surgical tool of claim 9, further comprising a sled integral with the clamping member having at least one cam wedge, wherein the movement of the upper engagement surfaces of the first and second transverse protrusions of the lower transverse member of the clamping member along the surface of the first jaw and the movement of the third and fourth transverse protrusions of the upper transverse member of the clamping member through the elongated slot further causes:
the sled to ride along the support channel, and
the at least one cam wedge to cooperate with at least one staple pusher of the staple cartridge assembly to eject at least one of the staples from the staple cartridge assembly.

15. The surgical tool of claim 14, further comprising the clamping member being configured without a knife blade.

16. A surgical tool for performing robotic surgery, the surgical tool comprising:
a shaft having a proximal end and a distal end, the proximal end being removably associated with a robotic system; and
a tool assembly, the tool assembly comprising:
a clamping member comprising:
a lower transverse member comprising first and second transverse protrusions extending in substantially opposite directions, each of the first and second transverse protrusions having an upper engagement surface,
an upper transverse member comprising third and fourth transverse protrusions extending in substantially opposite directions, and
an upward extension extending between and connecting the lower transverse member and the upper transverse member substantially perpendicular to the lower transverse member and the upper transverse member, the upper transverse member and the lower transverse member being substantially transverse to the upward extension,
a first jaw comprising:
a proximal end,
a distal end,
the first jaw having a support channel between the proximal end of the first jaw and the distal end of the first jaw, the support channel being configured to receive a staple cartridge assembly, the staple cartridge assembly having at least one tab, a longitudinal slot, at least three rows of staples disposed on each side of the longitudinal slot, and a sled including at least one cam wedge, the at least three rows of staples on each side of the longitudinal slot being substantially parallel to the longitudinal slot, the first jaw further comprising at least one aperture along an edge of the first jaw, and the at least one tab of the staple cartridge being engageable with the at least one aperture of the first jaw, at least the at least one aperture and the at least one tab being configured to cooperate to removably and replaceably retain the staple cartridge assembly within the elongated channel to permit replacement of the staple cartridge assembly during a surgical procedure, and a surface of the first jaw having a longitudinal slot between the proximal end of the first jaw and the distal end of the first jaw, the surface of the first jaw being configured to engage with the upper engagement surfaces of the first and second transverse protrusions of the lower transverse member of the clamping member as the upward extension travels through the longitudinal slot such that the first and second transverse protrusions slide along the surface of the first jaw, a second jaw pivotable relative to the first jaw, the second jaw comprising:

a proximal end, a distal end, an anvil having at least one anvil surface, the at least one anvil surface having at least one staple forming pocket, and the anvil having an elongated slot between the proximal end of the second jaw and the distal end of the second jaw, the elongated slot being configured to receive the third and fourth transverse protrusions of the upper transverse member of the clamping member as the upward extension travels through the elongated slot, wherein movement of the clamping member along the first and second jaws such that the upper engagement surfaces of the first and second transverse protrusions of the lower transverse member of the clamping member move along the surface of the first jaw and the third and fourth transverse protrusions of the upper transverse member of the clamping member move through the elongated slot and causes at least one of:

the first and second jaws to clamp, and staples to be ejected from the staple cartridge assembly when a staple cartridge assembly is received within the support channel of the first jaw, and a connection mechanism connecting the tool assembly to the shaft, the connection mechanism comprising:

a first pivot axis being substantially perpendicular to a longitudinal axis of the shaft, wherein the tool assembly is pivotable about the first pivot axis with respect to the shaft, and a second pivot axis being substantially perpendicular to the first pivot axis, wherein the tool assembly is pivotable about the second pivot axis with respect to the shaft.

17. The surgical tool of claim 16, wherein the first jaw includes a staple cartridge assembly received within the support channel of the first jaw, the staple cartridge assembly defining a longitudinal slot, and having at least one tab at least three rows of staples disposed on each side of the longitudinal slot, a sled including at least one cam wedge, the at least three rows of staples on each side of the longitudinal slot being substantially parallel to the longitudinal slot, and the at least one tab of the staple cartridge assembly being engageable with the at least one aperture of the first jaw, at least the at least one aperture and the at least one tab cooperating to removably and replaceably retain the staple cartridge assembly within the support channel to permit replacement of the staple cartridge assembly during a surgical procedure.

18. The surgical tool of claim 17, wherein the tool assembly is rotatable about the longitudinal axis of the shaft.

19. The surgical tool of claim 17, wherein the movement of the upper engagement surfaces of the first and second transverse protrusions of the lower transverse member of the clamping member along the surface of the first jaw and movement of the third and fourth transverse protrusions of the upper transverse member of the clamping member through the elongated slot further causes:

the sled to ride distal to the clamping member along the support channel, and the at least one cam wedge to cooperate with at least one staple pusher of the staple cartridge assembly to eject at least one of the staples from the staple cartridge assembly.

20. The surgical tool of claim 16, further comprising the clamping member being configured without a knife blade.

* * * * *